US006268353B1

(12) United States Patent
Chaen et al.

(10) Patent No.: US 6,268,353 B1
(45) Date of Patent: Jul. 31, 2001

(54) METHOD FOR INHIBITING THE FORMATION OF VOLATILE ALDEHYDES INCLUDING THEIR RELATED COMPOUNDS AND/OR THE DECOMPOSITION OF FATTY ACIDS INCLUDING THEIR RELATED COMPOUNDS, AND USES THEREOF

(75) Inventors: Hiroto Chaen, Okayama; Kazuyuki Oku, Hiroshima; Yukio Uchida; Toshio Miyake, both of Okayama, all of (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 09/387,520

(22) Filed: Sep. 1, 1999

(30) Foreign Application Priority Data

| Sep. 3, 1998 | (JP) | 10-249741 |
| Oct. 30, 1998 | (JP) | 10-310084 |
| Nov. 27, 1998 | (JP) | 10-337143 |
| Jun. 1, 1999 | (JP) | 10-154258 |
| Aug. 17, 1999 | (JP) | 11-230939 |

(51) Int. Cl.$^7$ .................................. A61K 31/70
(52) U.S. Cl. ............................ 514/53; 514/23; 426/321; 426/331
(58) Field of Search .................. 514/23, 53; 426/321, 426/331

(56) References Cited

U.S. PATENT DOCUMENTS 3,741,776   6/1973   Mitsuhashi et al. .

FOREIGN PATENT DOCUMENTS

| 0628630 | 12/1994 | (EP) . |
| 0636693 | 2/1995 | (EP) . |
| 0690130 | 1/1996 | (EP) . |
| 2097004 | 10/1982 | (GB) . |
| 47-13699 | 4/1972 | (JP) . |
| 63-2439 | 1/1988 | (JP) . |
| 7170977 | 7/1995 | (JP) . |
| 7213283 | 8/1995 | (JP) . |
| 873482 | 3/1996 | (JP) . |

OTHER PUBLICATIONS

Kijun, et al., "Standards for Analysis for Oils and Fats," Oil Chemical Society of Japan, Tokyo pp. 2.4.12–71 and pp. 2.2.22–73 (1983).

Eisei, et al., "Standards Methods of Analysis for Hygienic Chemists," Pharmaceutical Society of Japan, pp. 338–340 (1990).

*Primary Examiner*—Elli Peselev
(74) *Attorney, Agent, or Firm*—Browdy & Neimark

(57) ABSTRACT

A method for inhibiting the formation of volatile aldehydes including their related compounds and/or the decomposition of fatty acids including their related compounds by incorporating trehalose and/or maltitol. Using the method, compositions such as foods, cosmetics, and pharmaceuticals comprising fatty acids can be prepared and stably stored for a relatively-long period of time without fear of forming volatile aldehydes and/or decomposing the fatty acids.

25 Claims, No Drawings

METHOD FOR INHIBITING THE FORMATION OF VOLATILE ALDEHYDES INCLUDING THEIR RELATED COMPOUNDS AND/OR THE DECOMPOSITION OF FATTY ACIDS INCLUDING THEIR RELATED COMPOUNDS, AND USES THEREOF

BACKGROUND OF THE INVENTION

1. Field of the Invention

The present invention relates to a method for inhibiting the formation of volatile aldehydes including their related compounds (hereinafter abbreviated as "volatile aldehydes", unless specified otherwise) and/or the decomposition of fatty acids including their related compounds (hereinafter abbreviated as "fatty acids", unless specified otherwise), and more particularly to a method for inhibiting the formation of volatile aldehydes and/or the decomposition of fatty acids, comprising a step of incorporating trehalose and/or maltitol into a product to be treated; compositions comprising fatty acids in which the formation of volatile aldehydes and/or the decomposition of fatty acids are inhibited; decomposition inhibitory agents for volatile aldehydes and/or the decomposition of fatty acids, which comprise trehalose and/or maltitol as an effective ingredient; and uses thereof.

2. Description of the Prior Art

It is known that fatty acids with a relatively-high purity scarcely smell and form their characteristic disagreeable deteriorated smells when irradiated with an ultraviolet ray, treated with heat, or allowed to stand in the air for a relatively-long period of time. For example, in the case of masking such a disagreeable smell of compositions comprising fatty acids such as fishery products and meats, there has long been employed a method for cooking the compositions using seasonings such as a Guinea pepper, Japanese horseradish, sansho, garlic, and ginger. The method, however, is not one for lowering the formation of a deteriorated smell of ingredients but for masking disagreeable smell by imparting thereto a strong stimulant taste or flavor, resulting in altering the original desirable flavor, taste, and color of the fatty acids as a demerit. Therefore, it has been required to improve the demerit. In the case of cleaned rice as another composition containing fatty acids, it is known that fatty acids are susceptible to deterioration in such a manner that, just after cleaning, a cleaned rice instantly loses its freshness to easily cause a smell of rice lees as a deteriorated smell. The level of such a smell is even considered as a criterion of freshness of cleaned rice or a standard of the stability of quality. Thus, an establishment of a method for inhibiting the smell of rice lees has been in a great demand.

Recently, a method has been used for inhibiting the to dispersion of deteriorated smells, to improve the aforesaid smell, using an inclusion action effected by cyclodextrins. However, disadvantageously, it is known that even excluding a deteriorated smell of ingredients is only temporary, because the once included ingredients are replaceable with other substances more susceptible to the inclusion action, resulting in an ineffective masking effect.

SUMMARY OF THE INVENTION

In view of the conventional drawbacks, the present invention was made based on a completely novel technical concept, and the present invention aims to establish the followings: A method for not masking the once-formed deteriorated smells but inhibiting the formation of a deteriorated smell of ingredients, particularly, inhibiting the formation of volatile aldehydes and/or the decomposition of fatty acids; a composition in which the formation of volatile aldehydes and/or the decomposition of fatty acids are inhibited by using the method; a novel inhibitory agent for the formation of volatile aldehydes and/or the decomposition of fatty acids; and uses thereof.

To overcome the above objects, the present inventors continued studying on the use of saccharides; they studied the influence of saccharides on their inhibitory effect on the formation of volatile aldehydes from fatty acids by coexisting saccharides and fatty acids as precursors of volatile aldehydes. As a result, they found that, as compared with other saccharides, trehalose and/or maltitol unexpectedly exerted a strong inhibitory effect on the formation of volatile aldehydes, and confirmed that the saccharides inhibited the formation of fatty acids as precursors of volatile aldehydes. Thus, they accomplished this invention; this invention was made based on a technical concept of inhibiting fundamentally the formation of volatile aldehydes per se through the study of the formation of a deteriorated smell of ingredients, particularly, volatile aldehydes. It has never been conceived such a technical concept; the present technical art is in itself novel. The present invention is quite novel in that it employs a construction of inhibiting the formation of volatile aldehydes and/or the decomposition of fatty acids by incorporating trehalose and/or maltitol into a product to be treated, and that there found no prior art that discloses or aims such a construction. In other words, the objects and constructions according to the present invention per se are novel, and the effects are also novel and outstanding.

DETAILED DESCRIPTION OF THE INVENTION

The first object of the present invention is to provide a method for inhibiting the formation of volatile aldehydes and/or the decomposition of fatty acids, characterized in that it comprises a step of incorporating trehalose and/or maltitol into a product to be treated; the second object of the present invention is to provide a composition containing fatty acids which the formation of volatile aldehydes and/or the decomposition of fatty acids are inhibited by preserving and/or processing products with fatty acids in the presence of trehalose and/or maltitol; and the third object of the present invention is to provide an inhibitory agent for inhibiting the formation of volatile aldehydes and/or the decomposition of fatty acids, comprising trehalose and/or maltitol as an effective ingredient; and uses thereof.

Any trehalose and/or maltitol can be used in the present invention independently of their origins and properties as long as they inhibit the formation of volatile aldehydes and/or the decomposition of fatty acids. The trehalose usable in the present invention includes, for example, those in the form of a syrup, hydrous crystal, and anhydrous crystal, which are arbitrarily preparable by the methods as disclosed in Japanese Patent Kokai Nos. 170,977/95 and 213,283/95. In particular, "TREHAOSE®", a high-purity hydrous crystalline trehalose commercialized by Hayashibara Shoji, Inc., Okayama, Japan, can be advantageously used. The maltitol usable in the present invention includes, for example, those in the form of a syrup and anhydrous crystal, which are preparable by the methods as disclosed in Japanese Patent Kokoku Nos. 13,699/72 and 2,439/88. In particular, "MABIT®", a crystalline maltitol anhydride commercialized by Hayashibara Shoji, Inc., Okayama, Japan, can be advantageously used. Mixtures obtained by mixing these commercially available trehalose and maltitol in an appropriate proportion, and those obtained by hydrogenating trehalose and maltose, as disclosed in Japanese Patent Kokai No. 73,482/96, can be arbitrarily used as compositions of trehalose and maltitol. The trehalose and/or maltitol usable in the present invention should not be in a relatively-high purity form, and if necessary they can be used in combination with one or more another saccharides as shown in the below as long as they do not hinder the inhibitory effect on the formation of volatile aldehydes and/or the decomposition of fatty acids; reducing sugars such as glucose, maltose, maltotriose, and maltotetraose; non-reducing saccharides such as sorbitol, maltotriitol, and maltotetraitol; cyclodextrins and their related compounds such as α-, β- and γ-cyclodextrins and derivatives thereof; and aqueous polysaccharides such as gum arabic, pullulan, and elsinan can be freely used.

The volatile aldehydes as referred to in the present invention mean compounds having aldehyde groups which are volatile under ambient temperature. Preferable examples of such aldehydes are those having carbon atom numbers of 10 or lower, i.e., saturated hydrocarbon aldehydes such as formaldehyde, acetaldehyde, propanal, butanal, pentanal, hexanal, octanal, nonanal, and decanal; unsaturated hydrocarbon aldehydes such as propenal, butenal, pentenal, hexenal, heptenal, octenal, nonenal, heptadienal, and decadienal.

The fatty acids as referred to in the present invention mean fatty acids and their salts and esters, which are substantially not volatile under ambient temperature. Preferable examples of such fatty acids are higher fatty acids having carbon atom numbers of 14 or higher, i.e., saturated fatty acids such as myristic acid, palmitic acid, stearic acid, arachidic acid, and behenic acid; and unsaturated fatty acids such as myristoleic acid, palmitoleic acid, oleic acid, linoleic acid, linolenic acid, arachidonic acid, eicosapentaenoic acid, and docosahexaenoic acid.

The above-identified salts of fatty acids include those in the form of salts composed of fatty acids and freely-usable metal salts such as potassium, sodium, calcium, and magnesium.

The above-identified esters of fatty acids are those in the form of esters which carboxyl groups of fatty acids are bonded to hydroxyl groups of alcohols, glycerins, and saccharides; The representative examples are oils and fats including triglyceride, phosphatide including lecithin, and emulsifiers or surfactants including monoglycerides, polyglycerides and sugar esters.

The oils and fats used in the present invention include those from plants such as a soybean oil, corn oil, wheat embryo bud oil, rice bran oil, rape oil, mustard oil, sesame oil, saffron oil, cottonseed oil, olive oil, palm oil, and cacao butter oil; those from animals such as a tallow, milk fat, lard, chicken fat, egg yolk oil, fish oil, whale oil, cod-liver oil, and bone oil; and hydrogenated oils thereof. They also include lipid-soluble vitamins such as vitamins A, D, E and K; oils and fats which coexist with lipid-soluble substances such as waxes, terpenoids, steroids, and carotenoids. The phosphatides usable in the present invention include lecithin, cephalin, lysolecithin, and lipid acid.

The present composition comprising a fatty acid and/or its related compound means those which contain the above-identified fatty acids including their derivatives in the form of salts and esters in an amount of at least about 0.1 w/w % with respect to the fatty acids (in the specification, the wording "w/w %" is represented only by "%", unless specified otherwise), and more preferably at least about 0.5%. The present composition can be used independently of its form such as a liquid, paste or solid.

Preferable examples of fatty acids are in the form of food products, cosmetics, pharmaceuticals, their materials and intermediates, and additives including emulsifiers.

The food products and their materials and intermediates include the above-mentioned fatty acids as long as they are administrable to humans and breeding animals orally and intubationally in their intact forms or processed forms suitable for supplementing energy, promoting their health and growth, preventing diseases, and promoting the treatment of diseases. Examples of such are agricultural products such as a raw fruit, juice, dried fruit, vegetable extract, powdered vegetable, processed fruits and vegetables such as a pickle, powdered soybean, soy milk, pasted seed of sesame, peanut, and corn, raw an (a bean jam), powdered koshi-an (a screened bean jam), sweet potato flour, and yam flour; intact and powdered seeds such as a raw sesame, unhulled rice, wheat, burley, adlay, soybean, corn, peanut, almond, coffee bean, and cocoa been; refined rices such as a refined rice, unhulled rice, prewashed-rice, refined burley, refined adlay, powdered soybean, soybean embryo bud powder, buckwheat flour, and corn flour; roasted seeds and their powders such as those of a sesame, unhulled rice, wheat, burley, adlay, soybean, corn, peanut, almond, coffee bean, and cocoa been; refined rices such as a refined rice, unhulled rice, prewashed-rice, refined burley, refined adlay, powdered soybean, unhulled soybean powder; agricultural products such as processed seeds including a powdery roast grain, kinako (a powdered soybean), and coarse cut coffee; fishery products such as a pasted sardine, oyster extract, sea urchin extract, split horse mackerel, and fish meat; livestock products such as a meat, milk, raw cream, and chicken meat and egg; pasted or liquid seasonings such as a soy sauce, miso, sauce, mayonnaise, and dressing; powdered seasonings such as those of a soy sauce, spice, and seasoned fish meal; Japanese confectioneries such as a gyuhi (a paste of processed grain and starch syrup), okaki (a confectionery of rice paste), cracked bean, fried bean, karinto (a Japanese fried confectionery), Japanese cracker, and pao de Castella; Western confectioneries such as a chocolate, chewing gum, bun, bread, cream confectionery, and refreshment; processed fruits, vegetables and cereals; frozen desserts such as an ice cream and sherbet; teas such as a green tea, roasted tea, tea, oolong tea, unhulled rice tea, wheat tea, adlay tea; processed rice products such as a cooked rice, steamed rice, rice paste, rice ball, gruel, pre-gelatinized rice, Chinese dish of fried rice, and pilaf; processed confectioneries and breads; processed wheat products such as a pasta, noodle, pizza, naan, flour, and premix; processed soybeans such as a soybean milk, tofu (a bean curd), thick bean curd fried without using a coating, tofu refuse, hamburger made from tofu curd refuse, and pudding made from soybean milk; fermented foods such as koji, sweet drink made from fermented rice, sake, sweetened sake, beer, distilled alcohol, vinegar, miso, soy sauce, food picked with sake refuse, koji, rice bran cake, miso, and "tamarizuke" (a food soaked in soy sauce); processed meat products such as a hum and sausage; pasted fish meat products including relishes such as a boiled fish paste, "chikuwa" (a bamboo wheel shaped kamaboko), and fish cake; relishes such as a "uni-no-shiokara" (salted guts of sea urchin), "ika-no-shiokara" (salted guts of squid), dried meat and fish, "tsukudani" (a food boiled down in soy sauce)

of small fishes, shrimps, squids, shellfishes and meats, grilled bean, salad, fries, fried foods, boiled foods, egg roll, roast meat, roast chicken, hamburger, fried dumpling stuffed with minced pork, fried foods, and lees of tempura; processed milk products such as a condensed milk, milk powder, yogurt, butter, cheese, coffee milk; processed egg products such as bavarois, mousse, marshmallow, pudding, chou à la creme, stripped fried egg, seasoned fried egg, pot-steamed hotchpotch, and mayonnaise; bottled and canned products of meat, fish meat, and chicken egg; beverages of tea such as those produced with teas; refreshing beverages such as a coffee beverage, milk beverage, and lactic acid bacteria beverage; alcohols such as a sake, wine, and liquor; instant foods such as an instant wheat vermicelli, instant Chinese noodle, pudding premix, hot cake premix, instant soup, retort food, powdered food, and snack food; frozen foods, baby foods, therapeutic foods, health foods, and peptide foods; and materials of feeds and compositions thereof such as a cereal pellet, powdered cereal, oil cake, fermented cake, rice lees, wheat bran, burley bran, defatted bran, defatted soybean, fish meal, fish soluble, powdered meat, powdered blood, powdered feather, skim milk, and dried whey; chrysalis cake, and alfalfa-meal. The emulsifiers used in the present invention include additives such as sucrose fatty acid ester, glycerin mono-fatty acid ester, and sorbitan fatty acid ester.

The cosmetics according to the present invention include those which comprise fatty acids in the form of a liquid, paste or solid such as a tooth paste, lipstick, lip cream, cachou, gargle, bath salt, sweat-controlling agent, soap, shampoo, hair rinse, body soap, body lotion, deodorant spray, hair cream, skin beautifying agent, hair beautifying agent, and hair restorer.

The pharmaceuticals according to the present invention include those which comprise fatty acids in the form of a liquid, paste or solid such as a drink, oral nutrition, intubation nutrition, injectable fatty acid emulsion, troche, cod-liver oil drop, ointment, tablet, and capsule.

The wording "incorporating into products to be treated" means "to be coexisted by contact". In the case of incorporating trehalose and/or maltitol into compositions comprising fatty acids, any of methods can be used as long as they effectively inhibit the formation of volatile aldehydes including their related compounds from the compositions and/or effectively inhibit the decomposition of fatty acids. Preferably, trehalose and/or maltitol should be contacted with fatty acids as homogeneously as possible to be coexisted. In the case of using fatty acids in a juicy form like a liquid or paste, they can be mixed with trehalose and/or maltitol in the form of a solid such as a powder or crystal as homogeneously as possible or mixed with trehalose and/or maltitol in the form of a syrup as homogeneously as possible.

As for the compositions comprising fatty acids in a solid form, they can be prepared with water into liquid or paste products, then trehalose and/or maltitol are incorporated into the above products similarly treated as above or allowed to coexist together with the compositions in such a manner that trehalose and/or maltitol are prepared into syrups, and then dispersed and dissolved therein to allow them to contact with the compositions as homogeneously as possible. When the compositions are in a moistened solid form, they can be directly or after being pre-treated such as mincing, etc., sprayed with trehalose and/or maltitol in a powder or crystal form, and if necessary, they are adhered with, coated with and/or incorporated by permeating the trehalose and/or maltitol thereunto after being dissolved or melted, or the saccharide(s) is/are incorporated into the compositions as homogeneously as possible by soaking in syrups containing the saccharide(s). By spraying over the compositions aqueous saccharide solutions containing trehalose and/or maltitol, they can be arbitrarily coated therewith as homogeneous as possible. If necessary, the resulting products can be treated by dryings such as vacuum-, ventilation-, and spray-dryings, as well as dehydration treatments using anhydrous saccharides; and the incorporated trehalose and/or maltitol can be arbitrarily crystallized.

When the compositions containing fatty acids are fatty acid esters such as oils and fats including triglyceride, phosphatides including lecithin, emulsifiers, i.e., surfactants including sugar ester, the formation of volatile aldehydes and/or the decomposition of fatty acids in the compositions can be advantageously prevented by incorporating trehalose and/or maltitol when treated with processings of stirring, mixing, heating, pressing, emulsifying, pulverizing, and drying.

In the case of using, as the composition containing fatty acids, fishery products including fishes such as sardines, herrings, mackerels, yellowtails, flatfishes, and flounders; spawns such as salmon roes, tarako (spawns of Alaska pollack), and herring roes; mollusks such as cuttlefishes and octopuses; cruschymata such as lobsters, shrimps, prawns, and squilae; shellfishes such as short-necked clams, corbiculas, ear shells, and whelks, they can be incorporated with trehalose and/maltitol in the form of a powder, crystal or syrup when they are dried, soaked, grilled, boiled, steamed, fried, roasted, etc., to inhibit the formation of volatile aldehydes and/or the decomposition of fatty acids.

In the case of using, as the composition containing fatty acids, seeds for edible oils such as soybeans, rapeseeds, poppies, sesames, and peanuts; cereals such as rices, wheats, burleys, ryes, adlays, millets, and buckwheats; beans such as soybeans, peanuts, broad beans, and peas; seeds for refreshment such as almonds, cashew nuts, macadamia nuts, coffee beans, and cacao beans, they can be incorporated with trehalose and/maltitol in the form of a powder, crystal or syrup when they are refined, powdered, extracted for oils, steamed, roasted, etc., to inhibit the formation of volatile aldehydes and/or the decomposition of fatty acids. For example, as for rices unhulled rice is successively incorporated with trehalose and/or maltitol, stored, preserved in a usual manner, and refined with a rice refiner into a high-quality cleaned rice which the formation of volatile aldehydes and/or the decomposition of fatty acids are well inhibited. Such a high-quality cleaned rice can be also obtained by incorporating trehalose and/or maltitol into cleaned rice just after refined in a usual manner. The cleaned rice thus obtained, which the formation of rice bran smell and the lowering of freshness are satisfactorily inhibited, it can be used as a prewashed rice, pre-gelatinized rice, flavorful cooked rice, steamed rice, rice paste, rice ball, gullet, Chinese dish of fried rice, and pilaf. Using as main ingredients the aforesaid steamed rice and koji prepared therewith, fermented food products such as a sweet drink made from fermented rice, sake, sweetened sake, vinegar, miso, and soy sauce can be arbitrarily prepared. Referring to sake as an example, the aforesaid cleaned rices with an increased purity are steamed in a usual manner and used to prepare koji according to the method in Example B-14. Then, with the steamed rice and koji as main ingredients, sake yeasts are allowed to proliferate therewith to obtain a crude sake. To the crude sake the above steamed rice and koji together with water are successively added in three steps to saccharify and ferment the contents, followed by filtering the resultant mixture into a high-quality flavorful sake.

In the case of using, as the composition containing fatty acids, the following foods, they can be incorporated with trehalose and/or maltitol in the form of a powder, crystal or syrup when they are dried, soaked, grilled, boiled, steamed, etc., to inhibit the formation of volatile aldehydes and/or the decomposition of fatty acids; Fruits such as a lemon, yuzu (a Chinese lemon), sudachi (a kind of citrus fruit), zabon (shaddock), kumquat, banana, pineapple, mango, Chinese gooseberry, strawberry, hawthorn, blueberry, grape, peach, Japanese plum, apple, pear, and persimmon; rootcrops such as a carrot, Indian lotus, onion, edible burdock, radish, taro, yam, sweet potato, and potato; vegetables such as a lettuce, wild chicory, cabbages including Chinese cabbage, kale, Jew's marrow, ashitaba (a plant of Oenanthe javanica), spinach, komatsuna (a kind of Chinese cabbage), nozawana (a kind of turnip), garland chrysanthemum, chingensai (a Chinese vegetable), turnip, young leaves of teas and beefsteak plants, okura, cauliflower, broccoli, egg plant, tomato, cucumber, pumpkin, zucchini, sweet pepper, field pea, garden bean, and green soybean; and another vegetables including mushrooms such as a Japanese mushroom, velvetstemmed agaric, and oyster mushroom. For example, referring to the case of using as seed foods banana, mango, pumpkin, carrot, potato, kidney bean, etc., they are pealed, cut into appropriate sizes, incorporated with trehalose and/or maltitol, and if necessary after blanched and/or coated, treated with or without freezing, fried using food oils and fats under a normal or reduced pressure to obtain high-quality fried foods such as snack foods, fried noodles, daily dishes, materials for processing confectioneries and bakeries, and ingredients of instant foods.

The timing for incorporating trehalose and/or maltitol in the processings of compositions containing fatty acids is not specifically restricted, and any of one or more timings of before, during, and after the processings can be used as long as it attains the present inhibitory effects on the formation of volatile aldehydes and/or the decomposition of fatty acids. In cases of that the temperature of the compositions containing fatty acids increases during their processings, the saccharides are preferably incorporated into the compositions before or during their processings, or after the processings before sufficiently cooled down the contents.

In the case of using, as the composition containing fatty acids, seeds which are just after roasted and being in a relatively-high temperature such as a parched rice, parched wheat, parched bean, cracked corn, roasted cocoa bean, roasted coffee bean, and instant noodles and snacks which are just after fried and being in a relatively-high temperature, they are sprayed with an adequate amount of an aqueous trehalose and/or maltitol solution to incorporate the saccharide(s) thereunto and to instantly generate vapors and to eliminate evaporation heat, followed by eliminating or shielding air from the compositions to increase the level of the inhibitory effect on the formation of volatile aldehydes and/or the decomposition of fatty acids.

The amount of trehalose and/or maltitol to be incorporated is an amount effective for inhibiting the formation of volatile aldehydes and/or the decomposition of fatty acids, and is not specifically restricted. Usually, at least about 0.01%, preferably at least about 0.1% but less than about 98%, and more preferably at least about 1.0% but less than about 90% of trehalose and maltitol in total, on a dry solid basis (d.s.b.), are preferably incorporated into compositions comprising fatty acids. In general, when used in an amount of less than 0.01%, trehalose and/or maltitol could not sufficiently inhibit the formation of volatile aldehydes and/or the decomposition of fatty acids. When used over 30% of trehalose and/or maltitol in fatty acids as foods, it tends to over sweeten the foods. When required no care for sweetening or rather requiring for it, for example, in the case of relishes processed by using the compositions comprising fatty acids, refreshment-like foods, Western-type foods, trehalose and/or maltitol in an amount of over 30% can be advantageously incorporated thereunto or in a highest possible amount to crystallize the saccharides into hydrous crystalline trehalose and/or anhydrous crystalline maltitol, yielding products with a lesser hygroscopicity and a satisfactory stability.

According to the present method, an inhibitory agent for inhibiting the formation of volatile aldehydes and/or the decomposition of fatty acids (hereinafter may be abbreviated as "inhibitory agent") can be arbitrarily incorporated into compositions comprising fatty acids to attain a desired inhibitory effect. When used as an inhibitory agent, trehalose and/or maltitol is used in an amount that effectively inhibits the formation of volatile aldehydes and/or the decomposition of fatty acids, usually, the total content of saccharides is at least about 10%, preferably at least about 20%, and more preferably about 50%, d.s.b., to the inhibitory agent. The present inhibitory agent can be trehalose and/or maltitol alone, and if necessary the saccharides can be used in combination with one or more another substances among the aforesaid reducing saccharides, non-reducing saccharides, cyclodextrins, water soluble polysaccharides, spices, acids, tastes, alcohols, inorganic salts, and substances with an active-oxygen eliminating activity and chelating activity, resulting in an enhancement of the above inhibitory effects and in a further exertion of a masking effect. If necessary, an adequate amount of conventional flavors, colors, preservatives, stabilizers, etc., can be arbitrarily used in combination. Independently of shapes, the inhibitory agent thus obtained can be used in any of the form of a syrup, powder, crystal, granule, and tablet. The inhibitory agent can be used independently of the methods used as long as they exert an inhibitory effect on the formation of volatile aldehydes and/or the decomposition of fatty acids. For example, the agents can be used in accordance with the method used to inhibit the formation or the decomposition of volatile aldehydes and/or fatty acids formed from compositions comprising fatty acids into which the trehalose and/or maltitol are incorporated; After incorporating the inhibitory agent into the compositions, the resulting compositions are treated, for example, with preservation under ambient temperature or cooling conditions and/or cooking such as drying, soaking, roasting/grilling, boiling, steaming, frying, etc., and processings such as stirring, mixing, separating, heating, pressing, etc. By using similarly as the method for incorporating trehalose and/or maltitol as used in the above, the saccharides as effective ingredients used in the compositions effectively and arbitrarily exert an inhibitory effect on the formation of volatile aldehydes and/or the decomposition of fatty acids. The present inhibitory agent can effectively inhibit the formation of volatile aldehydes from compositions comprising fatty acid and/or the decomposition of fatty acids by using in combination with seasonings such as a soy sauce, miso, sauce, sauce for roast meat, ketchup, mayonnaise, dressing, margarine, butter, cheese, salad oil, oil for frying, sesame oil, layou, oyster oil, pasted Japanese horseradish, pasted mustard, grated ginger, vinegar, sweet drink made from fermented rice, synthetic sweetened sake, sake, wine, seasonings of amino acids and/or nucleic acids, and salt. In the case of producing seasonings such as those containing mayonnaise, dressing, etc., the present inhibitory agent arbitrarily facilitates to prepare seasonings with a satisfactory color, flavor, taste, and shelf-life by incorporating thereunto.

By using the present inhibitory agent in combination with materials and intermediates of cosmetics and pharmaceuticals, high-quality and stable cosmetics and pharmaceuticals can be arbitrarily prepared while effectively inhibiting the formation of volatile aldehydes and/or the decomposition of fatty acids. More particularly, in such cosmetics, they in themselves stably maintain their high-quality and inhibit the formation of volatile aldehydes from sweat, dirt, dandruff, and skin fat which are adhered to the skin and hair and/or the decomposition of fatty acids therefrom; they can be advantageously used to prevent the formation of body smell, less stimulate the skin, less cause itches, and treat/prevent adisonisms such as dyspigmentation, liver spots, freckles, and sunburn.

The following experiments describe the present invention in detail. Experiments 1 to 4 describe the influence of coexisting saccharides on the formation of volatile aldehydes and/or the decomposition of fatty acids. Experiments 5 to 8 describe the influence of coexisting saccharides on the decomposition of fatty acids. Experiments 9 to 15 describe the influence of coexisting saccharides on the deterioration of fatty acids.

EXPERIMENT 1-1

Influence of the Coexisting Saccharide on the Formation of Volatile Aldehydes from α-Linolenic Acid and/or on Deteriorated Smell Formed Therefrom One hundred milligrams of α-linolenic acid, 0.5 g cellulose powder, and 0.25 ml of 0.6 M phosphate buffer (pH 6.0) were placed in a 20-ml vial, then admixed with one milliliter of a 5% aqueous solution containing either of seven types of 50 mg of anhydrous crystals of trehalose, maltitol, erythritol, sorbitol, sucrose, maltose and neotrehalose. As a control, another vial free of saccharide was provided. These vials were sealed with a rubber stopper and treated by heating at 100° C. for one hour, and then cooled under ambient temperature and heated for five minutes in an aluminum block preheated at 80° C., followed by sampling two milliliters of a head space gas (hereinafter abbreviated as "HSG") from each vial with a gas syringe and subjecting HSG to gas chromatography (hereinafter abbreviated as "GLC") for analysis of volatile aldehydes using the following apparatuses and conditions: "GC-14B", an apparatus for GLC commercialized by Shimadzu Corporation, Tokyo, Japan; "TC-FFAP", a capillary column for analysis, 0.53 mm in diameter, 30 m in length, and 1.0 µm thickness, commercialized by GL Sciences Inc., Tokyo, Japan; helium gas as a carrier gas at a flow rate of 10 ml/min; 200° C. as an injection temperature; the conditions of column oven temperature—after keeping at 40° C. for five minutes, it was heated up to 230° C. at a rate of 5° C./min; and a hydrogen flame ionization detector as a detector. Six veteran panels conducted a sensory test for deteriorated smell of test samples in such a manner that they directly smell them. In the test, the results were evaluated based on the number of panels who answered the samples with saccharides had substantially the same, stronger, or lesser deteriorated smell than that of the sample with no saccharide.

Analytical data on HSG and evaluation results from the sensory test were tabulated in Table 1.

TABLE 1

| Saccharide | Concentration of volatile aldehydes in HSG from α-linolenic acid | | | Sensory evaluation on deteriorated smell |
|---|---|---|---|---|
| | Propanal | Butanal | Hexanal | |
| None | 10.0 | 0.23 | 0.11 | +++ |
| Trehalose | 1.27 | 0.07 | 0.02 | + |
| Maltitol | 2.44 | 0.08 | 0.02 | + |
| Erythritol | 8.60 | 0.24 | 0.09 | +++ |
| Sorbitol | 8.00 | 0.19 | 0.09 | +++ |
| Sucrose | 9.51 | 0.23 | 0.09 | +++ |
| Maltose | 9.40 | 0.19 | 0.10 | +++ |
| Neotrehalose | 8.60 | 0.19 | 0.08 | +++ |

In the table, the symbol "+++" represents that the number of panels, who answered the samples with saccharides had substantially the same and stronger deteriorated smells than that of the sample with no saccharide, was at least four among six panels; the symbol "+" represents that the number of panels, who answered the samples with saccharides had a lesser deteriorated smell than that of the sample with no saccharide, was at least four among six panels; and the symbol "++" represents between the above two evaluations.

As evident from the results in Table 1, it was revealed that the system where trehalose or maltitol were coexisted, particularly, the system with trehalose was superior because it showed an extremely lower concentration of propanal, butanal, or hexanal in HSG formed by heat decomposition of α-linolenic acid; and a significantly lesser deteriorated smell based on the sensory evaluation. On the sensory evaluation, the systems with another saccharides showed no difference as compared with the system with no saccharide, though some of the systems gave a rather lower concentration of volatile aldehydes in HSG.

EXPERIMENT 1-2

Influence of the Coexisting Saccharides on the Diffusion of Standard Volatile Aldehydes The following experiment was conducted to confirm the reason of the fact that the system with trehalose or maltitol in Experiment 1-1 showed a lower concentration of volatile aldehydes in HSG; whether it was caused by the inhibition of formation of volatile aldehydes from α-linolenic acid or the inhibition of diffusion of the formed volatile aldehydes. Using standard propanal, butanal, and hexanal as volatile aldehydes, the influence of coexisting trehalose, maltitol or sucrose was studied on the volatilization of these aldehydes; Ten milligrams of propanal, butanal or hexanal; 0.5 g cellulose powder; 0.25 ml of 0.6 M phosphate buffer (pH 6.0); and one milliliter of a 5% aqueous saccharide solution was placed in a 20-ml vial, sealed with a butyl rubber stopper, and heated for five minutes in an aluminum block preheated to 80° C., followed by collecting two milliliters of HSG with a gas syringe for analyzing volatile aldehydes on GLC. As a control, there provided a system free of saccharide, and then treated similarly as above.

The concentration (µg/ml) of each standard aldehyde volatilized into HSG in the systems with saccharides was assayed and converted into a relative concentration by regarding the concentration of the system free of saccharide as 100. The results were tabulated in Table 2.

TABLE 2

| Saccharide | Diffusion of volatile aldehydes as standards into HSG | | | | | |
|---|---|---|---|---|---|---|
| | Propanal | | Butanal | | Hexanal | |
| | (μg/ml) | (*RC) | (μg/ml) | (*RC) | (μg/ml) | (*RC) |
| Non | 9.25 | 100 | 8.34 | 100 | 7.25 | 100 |
| Trehalose | 9.07 | 98 | 8.59 | 103 | 7.90 | 109 |
| Maltitol | 8.79 | 95 | 8.42 | 101 | 7.11 | 98 |
| Sucrose | 9.34 | 101 | 8.23 | 99 | 7.40 | 102 |

Note: In the table, the symbol "*RC" represents "a relative concentration".

As evident from the results in Table 2, the system coexisted with trehalose or maltitol showed substantially the same level of relative concentration of propanal, butanal, and hexanal as standards in HSG as that of the system free of saccharide or the system with sucrose. Based on these results, the diffusion of propanal, butanal, and hexanal formed by heating α-linolenic acid was not prevented even in the presence of trehalose or maltitol, meaning that the diffusion well corresponded to the formation of volatile aldehydes. The deterioration smell inhibitory action by the coexisting trehalose or maltitol as the results in Table 1 was due to the inhibition of the formation of volatile aldehydes formed from α-linolenic acid by heating but not the masking effect by these saccharides. Particularly, it was revealed that the coexistence of trehalose advantageously inhibited the formation of volatile aldehydes.

EXPERIMENT 2

Influences of the Coexisting Saccharides on the Formation and/or the Deteriorated Smell from Linoleic Acid by Heating, and on the Diffusion of 2,4-Decadienal as a Standard Except for using linoleic acid as a fatty acid, it was treated by heating similarly as in Experiment 1-1, and the formed 2,4-decadienal as a main component of volatile aldehydes in HSG was measured on GLC. Similarly as in Experiment 1-1, a sensory test was conducted on deteriorated smell. In accordance with the method in Experiment 1-2, the influence of coexisting saccharides on the diffusion of 2,4-decadienal as a standard.

The concentration (μg/ml) of 2,4-decadienal in HSG and the relative concentration of the systems coexisted with saccharides were determined by regarding the concentration of the system free of saccharide as 100. The results were tabulated in Table 3.

TABLE 3

| Saccharide | 2,4-Decadienal from linoleic acid in HSG | | Sensory evaluation on | Diffusion of 2,4-decadienal as a standard into HSG | |
|---|---|---|---|---|---|
| | (μg/ml) | (*RC) | deteriorated smell | (μg/ml) | (*RC) |
| Non | 16.9 | 100 | +++ | 5.52 | 100 |
| Trehalose | 1.9 | 11 | + | 2.33 | 42 |
| Maltitol | 2.5 | 15 | + | 1.55 | 28 |
| Erythritol | 16.5 | 98 | +++ | 4.65 | 84 |
| Sorbitol | 15.1 | 89 | +++ | 5.32 | 96 |
| Sucrose | 15.9 | 94 | +++ | 5.44 | 99 |
| Maltose | 12.3 | 73 | +++ | 4.00 | 72 |
| Neotrehalose | 16.2 | 96 | +++ | 4.92 | 89 |

Note: In the table, the symbol "*RC" represents "a relative concentration". The symbol "+++" represents that "the number of panels, who answered the samples with saccharides had substantially the same level or stronger deteriorated smells than that of the sample with no saccharide, was at least four among the six panels"; the symbol "+" represents that "the number of panels, who answered the samples with saccharides had a lesser deteriorated smell than that of the sample with no saccharide, was at least four among the six panels; and the symbol "++" represents that "it lies between the above two evaluations".

As evident from the results in Table 3, in the case of 2,4-decadienal as a standard, there found a partial masking effect due to the fact that the systems coexisted with trehalose and maltitol showed relatively-low values of 42 and 28, respectively, as relative concentrations of 2,4-decadienal diffused into HSG. Moreover, it was revealed that trehalose and maltitol strongly inhibited the formation of 2,4-decadienal based on the fact that they showed much lower values of 11 and 15, respectively, as relative concentrations of 2,4-decadienal from linoleic acid diffused into HSG. Trehalose most superiorly inhibited the formation of 2,4-decadienal known as a characteristic unsatisfactory smell of chicken oils and meats.

EXPERIMENT 3

Influence of the Coexisting Saccharides on the Formation of Volatile Aldehydes from Plant Fatty-Acid-Containing Product A cleaned rice harvested in Fukui, Japan, in 1998, was used as a plant fatty-acid-containing product. Two hundred grams aliquots of the cleaned rice, just after the refining and kept at about 40° C., were placed in 500-ml polyethylene bags, 0.115 mm thickness, and admixed with four grams of anhydrous crystal of trehalose, maltitol, sorbitol, glucose, sucrose, maltose, or lactose. The resulting mixtures each were mixed as homogeneously as possible, sealed with a butyl rubber stopper, allowed to stand for cooling in an incubator kept at 25° C., and stored at the same temperature. After 2-weeks storage, five grams cleaned rice were sampled from each polyethylene bag and placed in a 20-ml vial, followed by cap-sealing the vial with a butyl rubber stopper. Then the vials were incubated for five minutes in an aluminum block preheated to 60° C., and one milliliter of HSG from each vial was sampled with a gas syringe and subjected to analysis for volatile aldehydes in HSG on GLC similarly as in Experiment 1-1 to calculate the level of volatile aldehydes formed from one gram of the cleaned rice after 2-weeks storage. Ten grams of the cleaned rice after 2-weeks storage were sampled, admixed with 10 ml deionized water (pH 6.64), and allowed to stand at 25° C. for 30 min, followed by measuring the pH of a supernatant by a pH meter. As a control, a system free of saccharide which only differed in this from the above systems was provided and treated similarly as above.

The results were tabulated in Table 4.

TABLE 4

| | Content of volatile aldehydes in HSG ($\mu$g/g cleaned rice) | | | | | |
|---|---|---|---|---|---|---|
| Saccharide | Propanal | Butanal | Pentanal | Hexanal | Total | pH |
| Non | 1157 | 358 | 7.3 | 0.31 | 1523 | 6.77 |
| Trehalose | 357 | 68 | 3.4 | 0.00 | 428 | 6.90 |
| Maltitol | 548 | 39 | 7.2 | 0.05 | 594 | 6.88 |
| Sorbitol | 800 | 279 | 7.0 | 0.07 | 1086 | 6.80 |
| Glucose | 720 | 185 | 4.0 | 0.21 | 909 | 6.83 |
| Sucrose | 1007 | 330 | 7.7 | 0.24 | 1345 | 6.80 |
| Maltose | 764 | 54 | 4.2 | 0.07 | 822 | 6.85 |
| Lactose | 423 | 178 | 15.0 | 0.06 | 616 | 6.87 |

As evident from the results in Table 4, after two weeks of storing, the system coexisted with trehalose or maltitol showed an extremely lower formation level of volatile aldehydes in HSG than that of the system free of saccharide. It was revealed that the coexistence of trehalose or maltitol strongly inhibits the formation of volatile aldehydes during the storing of cleaned rice. Particularly, the system with trehalose formed no hexanal as a main ingredient of smells of rice lees and long-stored rice even after two-weeks storage. While the degree of inhibitory action by sorbitol, glucose, sucrose and maltose was far lower than those of the system with trehalose or maltitol. As compared with the systems with saccharides other than trehalose and maltitol, the system coexisted with lactose showed a lower level of total volatile aldehydes in HSG, but showed a rather higher level of pentanal than the system free of saccharide. Referring to the data of measured pHs, the system coexisted with trehalose or maltitol showed a higher pH level than that of the system with no saccharide, and another systems with saccharides other than trehalose and maltitol showed a relatively-lower pH level and even showed substantially the same level of pH as found in the system with no saccharide. When a cleaned rice just after the polishing and free of the addition of saccharide was treated similarly as above and measured for pH in a supernatant, resulting in a pH of 6.93. The fact revealed that the coexistence of trehalose and/or maltitol inhibits the reduction of pH of cleaned rice during storage. Thus the results in the above Experiment 3-1 show that trehalose and/or maltitol inhibit the lowering of freshness of cleaned rice and well maintain the freshness when coexisted therein.

EXPERIMENT 3-2

Influence of the Coexisting Trehalose on the Formation of Deteriorated Smell from Plant Fatty-Acid-Containing Product Unhulled rice was used as a plant fatty-acid-containing product. Five hundred grams of unhulled rice produced in Okayama, Japan, in 1998, were placed in 500-ml polyethylene bags, 0.115 mm thickness, and admixed with 10 g of pulverized anhydrous crystalline trehalose to homogeneously adhere the saccharide on the unhulled rice. Twenty grams aliquots of the resulting rice were respectively placed in 50-ml vials, sealed with a butyl rubber stopper, and stored in an incubator kept at 50° C. At 0 (at the beginning of the storage test), 7 and 14 days, one milliliter aliquots of HSG were sampled with a gas syringe for analyzing deteriorated smells as main ingredients in HSG by GLC similarly as in Experiment 1-1. As a control, a system free of saccharide which only differed in this from the above systems was provided and treated similarly as above.

The amounts of main volatile ingredients formed from one gram of the unhulled rice at storage days of 0, 7 and 14 in each system were quantified, and the results were tabulated in Table 5.

TABLE 5

| Storage | | Content of volatile aldehydes in HSG ($\mu$g/g unhulled rice) | | | | | |
|---|---|---|---|---|---|---|---|
| period (day) | Trehalose | Ethyl acetate | Ethanol | Ethanal | Propanal | Hexanal | Total |
| 0 | No | 0.00 | 94.1 | 0.00 | 32.9 | 0.00 | 127.0 |
| | Yes | 0.00 | 52.2 | 0.00 | 29.8 | 0.00 | 82.0 |
| 7 | No | 1.50 | 136.5 | 4.20 | 56.4 | 0.00 | 198.0 |
| | Yes | 0.00 | 72.9 | 2.29 | 30.8 | 0.00 | 106.0 |
| 14 | No | 2.99 | 232.8 | 7.88 | 120.7 | 2.40 | 366.8 |
| | Yes | 0.00 | 145.8 | 3.54 | 94.5 | 0.00 | 243.8 |

As evident from the results in Table 5, it was revealed that the system coexisted with trehalose during the storage of unhulled rice less formed ingredients for deteriorated smells comprising volatile aldehydes as compared with the system free of trehalose, and that the coexisting trehalose well inhibited the formation of ingredients of deteriorated smells. Based on the fact that the levels of ethanol among the volatile aldehydes with and without trehalose were respectively 52.2 and 94.1 $\mu$g/g unhulled rice at storage period day of 0, it was also confirmed that the coexisting trehalose exhibited a partial masking effect on the diffusion of ethanol and more remarkably inhibited the formation of ethanol in itself as the storage period prolonged.

EXPERIMENT 4

Influence of the Coexisting Saccharides on the Formation of Volatile Aldehydes from Animal Fatty-Acid-Containing Product Mackerel meat was used as an animal fatty-acid-containing product. The meat was minced with a mincer, and 10 g aliquots of which were placed in 50-ml vials. To the vials were added five milliliters of aqueous trehalose solutions with different concentrations, containing 0.5, 1 and 2 grams trehalose that were equal to 5, 10 and 20% to the meat by weight. The vials were sealed with a butyl rubber stopper and heated for 15 min in a water bath, and then cooled under ambient temperature, reheated for 5 min in an aluminum block preheated to 80° C., followed by sampling one milliliter of HSG with a gas syringe for analyzing volatile aldehydes, trimethylamine, and ethylmercaptan. The trimethylamine and volatile aldehydes excluding methanal were analyzed on GLC. For analysis of methanal and ethylmercaptan, using "GASTECH No.91L" and "GASTECH No.72L", gas detection tubes commercialized by GL Sciences Inc., Tokyo, Japan, respectively, five milliliters of HSG in vials were similarly treated as above and sampled with a gas syringe. The samples were respectively passed through the tubes to measure the concentration of methanal and ethylmercaptan. As a control, a system with no saccharide and another system containing 10% or 20% anhydrous crystalline sorbitol, as a comparative saccharide, with respect to the weight of the mackerel meat were similarly tested.

The content of volatile aldehydes formed from one gram of the meat in each system was quantified, and the results were tabulated in Table 6. While the content of trimethylamine and ethylmercaptan were quantified, and the results were in Table 7.

TABLE 6

Content of volatile aldehydes in HSG (ng/g mackerel meat)

| Saccharide | Methanal | Ethanal | Propanal | Hexanal | Heptanal |
|---|---|---|---|---|---|
| Non Trehalose | 712 | 673 | 171 | 58.6 | 10.4 |
| 5% | 157 | 188 | 79 | 13.6 | 3.1 |
| 10% | 130 | 107 | 34 | 8.5 | 1.7 |
| 20% | 76 | 64 | 25 | 7.0 | 1.7 |
| Sorbitol |  |  |  |  |  |
| 10% | 454 | 363 | 121 | 26.4 | 6.3 |
| 20% | 266 | 144 | 97 | 20.2 | 3.8 |

TABLE 7

Content of volatile ingredients in HSG

| Saccharide | Trimethylamine | Ethylmercapatan |
|---|---|---|
| Non Trehalose | 8.71 | 105 |
| 5% | 4.90 | 42 |
| 10% | 1.58 | 39 |
| 20% | 0.64 | 31 |
| Sorbitol |  |  |
| 10% | 7.61 | 113 |
| 20% | 5.66 | 80 |

As evident from the results in Table 6, it was revealed that the system with trehalose extremely less formed both the volatile aldehydes in HSG as compared with both the system with no saccharide and one with sorbitol used widely in fishery processings such as sausages and fish pastes. It was revealed that the heating fish meats in the presence of trehalose extremely inhibited the formation of volatile aldehydes, and the effect increased depending on the amount of trehalose added. As evident from the results in Table 7, it was also found that the coexisting trehalose strongly inhibited the formation of trimethylamine and ethylmercapatan which were characteristic smells of fishery products, and that the effect increased depending on the amount of trehalose added.

EXPERIMENT 5

Influence of the Coexisting Saccharides on the Decomposition of Linoleic Acid by Light Irradiation One hundred milligrams of linoleic acid, 0.5 g cellulose powder, 0.25 ml of 0.6 M phosphate buffer (pH 6.0), and one milliliter of a 5% aqueous solution of anhydrous crystal of trehalose, maltitol, or sucrose as saccharides were placed in 20-ml vials. The vials were sealed with a butyl rubber stopper and irradiated at a luminous intensity of 3,200 lux using a fluorescent lump in an incubator kept at 25° C. The samples in each vial were sampled at prescribed time intervals, and linoleic acid in the samples was methylesterified by the method as indicated in the below and quantified on GLC; To the vials were added 20 ml of a mixture solution of chloroform and methanol (=2:1 by volume) to extract linoleic acid, and one milliliter of each of the resulting extracts was placed in a 10-ml egg plant type flask, and concentrated under a reduced pressure for drying into a solid. The solid was admixed with and dissolved in one milliliter solution of 30 mg/ml 1-eicosanol in methanol as an internal standard substance, dried again, and admixed with one milliliter solution of boron trifluoride in methanol, followed by sealing the flask and reacting the contents for five minutes in water bath. After cooling the reaction mixture, one milliliter of deionized water was added to the contents to decompose the remaining intact boron trifluoride, and admixed with one milliliter of n-hexane to extract linoleic acid methyl ester. Two micro-milliliters of the formed layer of n-hexane were subjected to GLC analysis. Based on the content of linoleic acid before and after the irradiation, the decomposition percentage of linoleic acid by irradiation was determined by the following equation. As a control a system with no saccharide was provided and treated similarly as above.

Equation:

$$Decomposition\ percentage\ (\%) = \frac{A - B}{A} \times 100$$

A: Linoleic acid content before irradiation

B: Linoleic acid content after irradiation

The apparatuses and conditions used in the GLC analysis were as follows: "GC-14B", a GLC apparatus commercialized by Shimadzu Corporation, Tokyo, Japan; "TC-FFAP", a capillary column as an analytical column, 0.53 mm in diameter, 30 m in length, 1.0 $\mu$m thickness, commercialized by GL Sciences Inc., Tokyo, Japan; helium gas as a carrier gas, a flow rate of 10 ml/min; injection temperature, 230° C.; column oven temperature, 120° C. for two minutes, then heated up to 230° C. at a rate of 5° C./min; and detection using a hydrogen flame ionization detector.

The results were tabulated in Table 8.

TABLE 8

Decomposition percentage of linoleic acid (%)

| Saccharide | 1 day | 5 days | 7 days | 14 days |
|---|---|---|---|---|
| Non | 20.6 | 38.0 | 46.4 | 56.6 |
| Trehalose | 5.7 | 23.6 | 29.9 | 39.8 |
| Maltitol | 6.9 | 25.0 | 31.5 | 41.2 |
| Sucrose | 14.8 | 40.5 | 49.7 | 57.0 |

As evident from the results in Table 8, referring to the influence of light irradiation on the decomposition of linoleic acid, the system coexisted with trehalose or maltitol, particularly, one with trehalose was superior to the system with no saccharide in that it less decomposed linoleic acid than the system with no saccharide and strongly inhibited the decomposition. No such an effect was found in the system with sucrose.

EXPERIMENT 6

Influence of the Coexisting Saccharide on the Decomposition of Linoleic Acid by Heating One hundred milligrams of linoleic acid, 0.5 g cellulose powder, and 0.25 ml of 0.6 M phosphate bufferred saline, one milliliter of a 0–5 w/v % aqueous saccharide solution containing 0, 12.5, 25.0 or 50 mg of anhydrous crystal of trehalose, maltitol or sucrose were placed in 20-ml vials. The vials were sealed with a butyl rubber stopper, heated at 100° C. for one hour, and cooled to ambient temperature. Similarly as in Experiment 5, linoleic acid after the heat treatment was quantified on GLC. Based on the linoleic acid content before and after the heat treatment, the decomposition percentage (%) of linoleic acid by heating was determined in accordance with the method in Experiment 5.

The results were tabulated in Table 9.

TABLE 9

| Saccharide | Saccharide added mg | Decomposition percentage (%) of linoleic acid |
| --- | --- | --- |
| Non | — | 59.0 |
| Trehalose | 12.5 | 44.3 |
|  | 25.0 | 32.4 |
|  | 50.0 | 22.3 |
| Maltitol | 12.5 | 49.7 |
|  | 25.0 | 42.2 |
|  | 50.0 | 31.6 |
| Sucrose | 12.5 | 57.7 |
|  | 25.0 | 57.7 |
|  | 50.0 | 57.0 |

As evident from the results in Table 9, referring to the influence of heating on the decomposition of linoleic acid, the system coexisted with trehalose or maltitol, particularly, one with trehalose was superior to the system with no saccharide in that it less decomposed linoleic acid than the system with no saccharide and strongly inhibited the decomposition. Such an effect was hardly found in the system with sucrose.

EXPERIMENT 7

Influence of the Coexisting Saccharide on the Decomposition of Higher Unsaturated Fatty Acid by Heating Except for using a 0.5 ml of methanol solution containing 100 mg eicosapentaenoic acid or docosahexaenoic acid as a higher unsaturated fatty acid, and one milliliter of a 5% aqueous solution containing 50 mg of anhydrous crystalline trehalose or anhydrous crystalline sucrose as a saccharide, test samples were treated by heating similarly as the method in Experiment 6. Higher unsaturated fatty acids before and after the heat treatment were quantified on GLC. Based on the amounts of higher unsaturated fatty acids before and after the heat treatment, the decomposition percentage (%) of higher unsaturated fatty acids by heating was determined in accordance with the method in Experiment 5.

The results were tabulated in Table 10.

TABLE 10

| | Decomposition percentage (%) of higher unsaturated fatty acid | |
| --- | --- | --- |
| Saccharide | Eicosapentaenoic acid | Docosahexaenoic acid |
| Non | 26.5 | 24.6 |
| Trehalose | 18.9 | 16.7 |
| Sucrose | 24.1 | 26.3 |

As evident from the results in Table 10, referring to the influence of heating on the decomposition of higher unsaturated fatty acids, the system coexisted with trehalose was superior to the system with no saccharide in that it less decomposed higher unsaturated fatty acids than the system with no saccharide and strongly inhibited the decomposition. Such an effect was hardly found in the system with sucrose.

EXPERIMENT 8

Influence of the Coexisting Saccharide on the Decomposition of Fatty Acids by Heating Except for using 100 mg of α-linolenic acid, linoleic acid, oleic acid, or stearic acid as fatty acids, one milliliter of a 5% aqueous solution containing 50 mg hydrous crystalline trehalose, anhydrous crystalline maltitol, anhydrous crystalline erythritol, anhydrous crystalline sorbitol, anhydrous crystalline sucrose, hydrous crystalline maltose, and hydrous crystalline neotrehalose as saccharides, test samples were treated by heating similarly as in Experiment 6. The fatty acids before and after the heat treatment were quantified on GLC. Based on the contents of the fatty acids before and after the heat treatment, the decomposition percentage (%) of fatty acids by heating was determined in accordance with the method in Experiment 5. The results were tabulated in Table 11.

TABLE 11

| | Decomposition percentage (%) of fatty acids | | | |
| --- | --- | --- | --- | --- |
| Saccharide | α-Linolenic acid | Linoleic acid | Oleic acid | Stearic acid |
| Non | 47.7 | 59.0 | 39.7 | 13.3 |
| Trehalose | 33.4 | 22.3 | 14.7 | 7.7 |
| Maltitol | 37.1 | 31.6 | 21.7 | 8.6 |
| Erythritol | 49.5 | 60.1 | 33.1 | 14.3 |
| Sorbitol | 40.5 | 57.0 | 31.0 | 10.7 |
| Sucrose | 50.8 | 57.0 | 36.6 | 13.3 |
| Maltose | 46.0 | 52.9 | 39.7 | 12.6 |
| Neotrehalose | 47.8 | 61.3 | 34.6 | 13.8 |

As evident from the results in Table 11, referring to the influence of heating on the decomposition of fatty acids, the system coexisted with trehalose or maltitol, particularly, one with trehalose was superior to the system with no saccharide in that it less decomposed linoleic acid than the system with no saccharide and strongly inhibited the decomposition. While the system coexisted with erythritol, sucrose, maltose or neotrehalose, no such an inhibitory effect was observed. The system with sorbitol inhibited the decomposition of α-linoleic acid and stearic acid by heating, but the level was far lower than those with trehalose and maltitol.

EXPERIMENT 9

Influence of the Coexisting Saccharides on the Heat Generation by Fatty-Acid-Containing Product It is known that, when allowed to stand under aerobic conditions, fatty-acid-containing products such as tempura refuses just after fried generate heat due to the decomposition of oils and fats contained therein, form volatile aldehydes, and even induce a spontaneous combustion. In view of this, it was examined the influence of coexisting saccharides on the heat generation on tempura refuses; A butter, consisting of 425 parts by weight of a wheat flour, 75 parts by weight of a corn starch, 25 parts by weight of a saccharide, 500 parts by weight of water, and five parts by weight of a baking powder, was prepared. Trehalose, glucose or sucrose was used as the saccharide. Each of the butters was fried with a salad oil heated to 180° C. to obtain tempura refuses. As a control, a butter free of saccharide was similarly fried as above to obtain tempura refuses. The resulting tempura refuses were allowed to stand overnight under cooling conditions and heated to ambient temperature. One hundred and eighty grams aliquots of each of the tempura refuses were respectively injected into an aluminum can, having an open-air top, a porous plate basement with holes of 0.4 mm in diameter, and a cylindrical shape of 5.6 cm in diameter and 16.7 cm in height. A thermocouple as a thermometer was inserted into the center of each can from the upper part thereof, covered outer sidewall of each can with a thermo-insulator made of glass wool, and placed in an incubator kept at 150° C. for measuring the temperature of tempura refuses at prescribed time intervals.

The results were tabulated in Table 12.

TABLE 12

| Saccharide | Time (hour) | | | | |
|---|---|---|---|---|---|
| | 0 | 2 | 3 | 4 | 5 |
| Non | 25° C. | 145° C. | 162° C. | 166° C. | 166° C. |
| Trehalose | 25° C. | 143° C. | 159° C. | 159° C. | 159° C. |
| Glucose | 25° C. | 145° C. | 163° C. | 168° C. | 169° C. |
| Sucrose | 25° C. | 145° C. | 164° C. | 170° C. | 170° C. |

As evident from the results in Table 12, the degree of heat generation due to the decomposition of oils and fats in tempura refuses varied depending on the saccharides contained therein. It was revealed that the increase of temperature of the tempura refuse with trehalose was more inhibited than that with glucose or sucrose, and without saccharide, and that the tempura refuse with trehalose less generated heat inducible by the decomposition of oils and fats than others, meaning that the tempura refuse with trehalose less generates heat inducible by the decomposition of oils and fats, and has a lesser fear of spontaneous combustion. Thus, the tempura refuse with trehalose would be a safer fatty-acid-containing product in view of the protection of fire.

EXPERIMENT 10

Influence of the Coexisting Saccharides on the Change of Fatty-Acid-Containing Product when Stored at Higher Temperatures Using tempura refuses containing saccharides as a fatty-acid-containing product, the influence of coexisting saccharides on the change of fatty-acid-containing product when stored at a higher temperature; According to the method in Experiment 9, three different types of tempura refuses containing different saccharides and a tempura refuse free of saccharide were prepared. Six grams aliquots of the four types of tempura refuses were placed in cans for weighing, allowed to stand in an incubator at 180° C. for 0, 1 or 3 hours, and then macroscopically observed on their coloration degree under each storage condition and weighed for calculating the weight change (%) with respect to the weight before and after the standing. The results were in Table 13.

TABLE 13

| | Preservation time (hour) | | | | | |
|---|---|---|---|---|---|---|
| | 0 | | 1 | | 3 | |
| Saccharide | Color | Weight change (%) | Color | Weight change (%) | Color | Weight change (%) |
| Non | Pale yellow brown | 0.0 | Brown | -0.5 | Dark brown | -2.3 |
| Trehalose | Pale yellow | 0.0 | Pale yellow brown | +0.5 | Pale brown | -1.5 |
| Glucose | Brown | 0.0 | Black | -2.3 | Black | -5.0 |
| Sucrose | Pale yellow brown | 0.0 | Dark black brown | -1.2 | Black | -3.5 |

As evident from the results in Table 13, when allowed to stand in the incubator kept at 180° C., the changes of color and weight of tempura refuses deferred depending on the saccharides used. The browning of the tempura refuse with trehalose was more inhibited than that with glucose or sucrose and without saccharide, and that the tempura refuse with trehalose less lowered in weight than the others. The data indicates that trehalose closely relates to the inhibition of the decomposition of oils and fats in tempura refuses and to the inhibition of the formation of volatile aldehydes.

EXPERIMENT 11

Influence of the Coexisting Saccharides on the Deterioration of Fatty-Acid-Containing Product Using mayonnaise as a fatty-acid-containing product, it was examined for the influence of coexisting saccharides on the change of the fatty-acid-containing product during preservation under light irradiated conditions. One part by weight of a saccharide was mixed with 20 parts by weight of a commercially available mayonnaise to dissolve the saccharide therein. As the saccharide, trehalose or sucrose was used. Twenty grams aliquots of the mayonnaise thus obtained were respectively placed in a transparent polyethylene bag, 120 mm×85 mm, 0.04 mm thickness. The bags were sealed, placed in an incubator kept at 25° C., and irradiated with a light having an intensity of 9,300 lux using a fluorescent lamp. From each bag mayonnaise was sampled at prescribed time intervals and measured for the amount of volatile aldehydes, peroxide value, and carbonyl value. The amount of volatile aldehydes was quantified by placing three grams of a sample in a 20-ml vial, sealing the vial with a butyl rubber stopper, incubating in an aluminum block preheated to 80° C. for five minutes, sampling two milliliters of HSG, and subjecting the sampled HSG to GLC under the following conditions: "GC-14B", an apparatus for GLC commercialized by Shimadzu Corporation, Tokyo, Japan; "SPERUCO-WAX", a capillary column for analysis, 0.25 mm in diameter, 60 m in length, and 2.5 μm thickness, commercialized by Speruco Inc., Tokyo, Japan; helium gas as a carrier gas at a flow rate of 1.0 ml/min; 250° C. as an injection temperature; conditions of column oven temperature—after keeping at 80° C. for five minutes, it was increased up to 240° C. at a rate of 5° C./min; and a hydrogen flame ionization detector as a detector.

The peroxide value and carbonyl value were respectively measured by applying the methods disclosed in pp.2.4.12–71 and pp. 2.4.22–73 in *Kijun-Yushi-Bunseki-Shiken-Ho* (Standard for Analysis for Oils and Fats), authorized by the Oil Chemical Society of Japan (1990), publish by the Oil Chemical Society of Japan, Tokyo, for samples obtained in accordance with the method in *Eisei-Shiken-Ho-Chukai* (Standard Methods of Analysis for Hygienic Chemists—With Commentary—), authorized by the Pharmaceutical Society of Japan (1990), published by Kanehara Publisher, Tokyo, Japan.

As a control, a system substantially the same as above one but free of a saccharide was provided and treated similarly as above. The results of the amount of volatile aldehydes, the peroxide value, and the carbonyl value were respectively tabulated in Tables 14, 15 and 16.

TABLE 16

| Coexisting saccharide | Carbonyl value* | | |
|---|---|---|---|
| | Starting of preservation | 3-days after preservation | 7-days after preservation |
| Non | 2.0 | 7.2 | 40.0 |
| Trehalose | 2.6 | 7.4 | 26.2 |
| Sucrose | 2.1 | 9.3 | 41.8 |

*Absorbance at a wavelength of 440 nm per one gram of a sample.

As evident from the results in Tables 14, 15 and 16, the system with trehalose exhibited lower values on the amount of volatile aldehydes, peroxide value, and carbonyl value as compared with the one with sucrose and the one free of saccharide. The deterioration degree of oils and fats in mayonnaise was inhibited by the coexisting trehalose. The data showed that the coexisting trehalose well inhibited the deterioration of a fatty-acid-containing product such as a mayonnaise when stored under light-irradiated conditions.

EXPERIMENT 12

Influence of the Coexisting Saccharide on the Deterioration of Fatty-Acid-Containing Product Using tempura refuses containing saccharides as a fatty-acid-containing product, the influence of coexisting saccharides on the preservation at 25° C. under light-shielded conditions. In accordance with the method in Experiment 9, a tempura refuse, which contained a saccharide selected from trehalose, maltitol, glucose, maltose and sucrose, and another tempura refuse free of saccharide were prepared. These tempura refuses were placed in transparent polyethylene bags, followed by sealing the bags and storing the bags in an incubator at 25° C. for 30 days under light-shielded conditions. The volatile aldehydes was quantified in such a

TABLE 14

| Preservation period (day) | Coexistence of saccharide | Content of volatile aldehydes in HSG (μg/g sample) | | | | | | | | |
|---|---|---|---|---|---|---|---|---|---|---|
| | | Ethanal | Propanal | Butanal | Pentanal | Hexanal | Octanal | Nonanal | Decanal | Total |
| 3 | Non | 0.0 | 85.3 | 0.0 | 0.0 | 1.8 | 2.9 | 5.8 | 2.0 | 97.8 |
| | T | 0.0 | 30.8 | 15.4 | 0.0 | 0.0 | 0.5 | 0.8 | 0.0 | 47.5 |
| | S | 0.0 | 84.2 | 0.5 | 0.0 | 1.5 | 3.1 | 5.5 | 1.8 | 96.6 |
| 7 | Non | 14.9 | 212.2 | 0.0 | 26.3 | 0.0 | 2.9 | 2.7 | 0.0 | 259.0 |
| | T | 0.0 | 33.2 | 13.6 | 5.3 | 0.0 | 0.7 | 1.0 | 0.0 | 53.8 |
| | S | 14.2 | 202.5 | 1.0 | 25.3 | 0.0 | 3.0 | 2.8 | 0.0 | 248.8 |

Note: The symbols "T" and "S" represent "trehalose" and "sucrose", respectively.

TABLE 15

| Coexisting saccharide | Peroxide value (meq/kg oils and fats) | | |
|---|---|---|---|
| | Starting of preservation | 3-days after preservation | 7-days after preservation |
| Non | 0.0 | 32.4 | 142.5 |
| Trehalose | 0.1 | 22.9 | 85.7 |
| Sucrose | 0.1 | 32.4 | 156.5 | manner that the tempura refuses were sampled at the initiation and 30 days after the preservation, and then disrupted. Five grams aliquots of each of the disrupted samples were respectively placed in 20-ml vials, followed by sealing the vials with a butyl rubber stopper, incubating the vials in an aluminum block preheated to 80° C., sampling two milliliters of HSG from each of the vials, and subjecting the samples to GLC under similar conditions as used in Experiment 11. The results were tabulated in Table 17.

TABLE 17

| Preservation period (day) | Coexisting saccharide | Content of volatile aldehydes in HSG ($\mu$g/g sample) | | | | | | | | |
|---|---|---|---|---|---|---|---|---|---|---|
| | | Ethanal | Propanal | Butanal | Pentanal | Hexanal | Octanal | Nonanal | Decanal | Total |
| 0 | Non | 0.00 | 4.19 | 4.70 | 0.22 | 0.00 | 0.30 | 1.28 | 1.18 | 11.87 |
| | Trehalose | 0.00 | 0.00 | 0.93 | 0.00 | 0.00 | 0.00 | 0.00 | 0.00 | 0.93 |
| | Maltitol | 0.00 | 1.43 | 1.88 | 0.00 | 0.36 | 0.10 | 0.44 | 0.00 | 4.21 |
| | Glucose | 0.00 | 9.07 | 3.88 | 0.66 | 0.71 | 0.67 | 2.75 | 1.64 | 19.38 |
| | Maltose | 0.00 | 6.31 | 6.40 | 0.04 | 1.28 | 0.49 | 2.20 | 1.38 | 18.10 |
| | Sucrose | 0.00 | 5.12 | 3.70 | 0.28 | 1.33 | 0.38 | 1.46 | 0.58 | 12.85 |
| 30 | Non | 0.00 | 9.71 | 10.74 | 0.00 | 3.01 | 0.86 | 3.14 | 1.16 | 28.62 |
| | Trehalose | 0.00 | 1.37 | 0.75 | 0.00 | 0.00 | 0.20 | 0.43 | 0.00 | 2.75 |
| | Maltitol | 0.45 | 1.47 | 2.10 | 0.00 | 0.00 | 0.30 | 0.64 | 0.00 | 4.96 |
| | Glucose | 2.19 | 7.02 | 16.84 | 1.13 | 2.95 | 1.29 | 4.56 | 1.79 | 37.77 |
| | Maltose | 2.29 | 4.26 | 9.16 | 0.55 | 2.06 | 0.88 | 2.95 | 0.87 | 23.02 |
| | Sucrose | 2.03 | 3.93 | 2.52 | 0.43 | 1.54 | 0.67 | 2.36 | 0.68 | 14.16 |

As evident from the results in Table 17, the formation of volatile aldehydes from tempura refuses changed depending on the types of coexisting saccharides during processings and preservation after processings. The tempura refuse with trehalose formed the minimum level of volatile aldehydes, meaning that trehalose most satisfactorily inhibited the formation of volatile aldehydes, and the next was maltitol. The coexistence of glucose more formed volatile aldehydes and promoted the formation than the system free of saccharide as a control.

EXPERIMENT 13

Influence of the Coexisting Saccharide on the Deterioration of Fatty-Acid-Containing Product Roasted and sliced almonds containing trehalose or sucrose as a fatty-acid-containing product were stored at 25° C. for 14 days for examining the influence of coexisting saccharides on the deterioration of fatty-acid-containing product. Commercially available sliced almonds, about one millimeter thickness, were soaked in an about 70% aqueous trehalose solution, incubated at 70° C. for 10 min, drained, and roasted at 160° C. or 180° C. using an electric oven. In place of the trehalose, an aqueous sucrose solution, as a saccharide, kept at the same temperature and concentration as the above aqueous trehalose solution, the commercially available sliced almonds were roasted similarly as above. Four grams aliquots of the two types of sliced almonds were placed in polyethylene bags, followed by sealing the bags and storing the bags in an incubator kept at 25° C. for 14 days under light-shielded conditions. Using these roasted almonds as samples, they were similarly treated as above for quantifying volatile aldehydes. The results were in Table 18.

As evident from the results in Table 18, the formation level of volatile aldehydes from roasted almonds changed depending on the types of coexisting saccharides during roasting and preservation after roasting. The system with trehalose less formed volatile aldehydes than that with sucrose, revealing that trehalose satisfactorily inhibited the formation of volatile aldehydes.

EXPERIMENT 14

Influence of the Coexisting Saccharide on the Deterioration of Fatty-Acid-Containing Product Fried carrots containing trehalose or maltose as a fatty-acid-containing product were stored at 40° C. for 14 days for examining the influence of coexisting saccharide on the deterioration of fatty-acid-containing product; A carrot was pealed, subjected to a slicer into sliced carrots, about five millimeters thickness, and blanched for three minutes in water heated to 95° C. and containing 18% trehalose or maltose with respect to a saccharide concentration. As a control, a system free of saccharide was similarly blanched as above. The resulting carrots were in a usual manner fried in vacuo in a food oil to obtain a fried carrot containing trehalose or maltose, and one free of saccharide as a control. Five grams aliquots of the two types of fried carrots were placed in 20-ml vials, followed by sealing the vials with a butyl rubber stopper and storing the vials in an incubator kept at 40° C. for 14 days under light-shielded conditions. The measurement for quantifying volatile aldehydes was done by treating similarly as in Experiment 12 at the initiation of storing and at 14 days after storing. The results were tabulated in Table 19.

TABLE 18

| Coexisting Saccharide | Roasting temperature | Content of volatile aldehydes in HSG ($\mu$g/g sample) | | | | | |
|---|---|---|---|---|---|---|---|
| | | Ethanal | Propanal | Butanal | Pentanal | Hexanal | Total |
| Sucrose | 160° C. | 0.00 | 0.95 | 10.10 | 4.80 | 3.00 | 18.85 |
| | 180° C. | 0.52 | 0.00 | 4.10 | 0.00 | 7.20 | 11.82 |
| Trehalose | 160° C. | 0.00 | 1.00 | 2.00 | 0.00 | 0.00 | 3.00 |
| | 180° C. | 0.00 | 0.90 | 3.40 | 0.00 | 0.00 | 4.30 |

TABLE 19

| Preservation period (day) | Coexisting saccharide | Content of volatile aldehydes in HSG (μg/g sample) | | | | | | | | |
|---|---|---|---|---|---|---|---|---|---|---|
| | | Ethanal | Propanal | Butanal | Pentanal | Hexanal | Heptanal | Octanal | Nonanal | Total |
| 0 | Non | 0.00 | 0.27 | 0.08 | 0.19 | 0.08 | 0.00 | 0.00 | 0.00 | 0.62 |
| | Trehalose | 0.05 | 0.00 | 0.00 | 0.00 | 0.00 | 0.00 | 0.00 | 0.00 | 0.05 |
| | Maltose | 0.00 | 0.00 | 2.31 | 1.16 | 0.04 | 0.03 | 0.03 | 0.00 | 3.57 |
| 14 | Non | 5.11 | 0.00 | 26.47 | 0.00 | 0.00 | 0.36 | 0.00 | 0.00 | 31.94 |
| | Trehalose | 0.00 | 0.00 | 7.33 | 0.00 | 0.00 | 0.00 | 0.00 | 0.00 | 7.33 |
| | Maltose | 2.21 | 2.22 | 10.26 | 0.00 | 0.00 | 0.07 | 0.00 | 0.12 | 14.88 |

As evident from the results in Table 19, the formation level of volatile aldehydes from fried carrots changed depending on the types of coexisting saccharides during frying and preservation after frying. The system with trehalose less formed volatile aldehydes than that with sucrose, revealing that trehalose satisfactorily inhibited the formation of volatile aldehydes.

EXPERIMENT 15

Influence of the Coexisting Saccharide on the Deterioration of Fatty-Acid-Containing Product Doughnuts containing trehalose and/or sucrose as a fatty-acid-containing product were kept at 30° C. for 7 and 14 days for examining the influence of coexisting saccharide on the deterioration of a fatty-acid-containing product. A dough for doughnut, containing trehalose and/or sucrose, was prepared by using a composition as shown in Table 20 and fried in a usual manner to obtain doughnuts. Four aliquots of the doughnuts, which had been sprayed with about one gram of a 50% aqueous trehalose or sucrose solution per a doughnut, about six grams, were placed in aluminum laminated bags, 17×10 cm, injected with air to bring the inner air volume to about 200 ml, and stored in an incubator at 30° C. for 7 and 14 days under light-shielded conditions.

TABLE 20

| | | Test No. | | | |
|---|---|---|---|---|---|
| | | 1 (Control) | 2 | 3 | 4 |
| Composition | Wheat flour | 300 | 300 | 300 | 300 |
| | Refined sugar, high grade | 90 | 40 | 40 | 90 |
| | Hydrous crystalline trehalose | 0 | 55 | 55 | 0 |
| | Egg | 100 | 100 | 100 | 100 |
| | Butter | 30 | 30 | 30 | 30 |
| | Baking powder | 10 | 10 | 10 | 10 |
| | Water | 60 | 55 | 55 | 60 |
| Aqueous saccharide solution | | Sucrose | Sucrose | Trehalose | Trehalose |

Note: In the table, numerals represent proportions in dough for doughnuts.
Hydrous crystalline trehalose had a moisture content of about 9.6%.

The content of volatile aldehydes was measured by placing bags with samples, which had been sampled at, 7 days after, and 14 days after the initiation of preservation, in an electric oven which had been previously heated to and kept at 80° C., and maintained at 80° C. for five minutes. Thereafter, two milliliters of HSG from each bag were sampled and subjected to GLC similarly as in Experiment 11. The results were tabulated in Table 21.

TABLE 21

| Preservation period (day) | Test No. | Content of volatile aldehydes in HSG (µg/g sample) | | | | | | | | | |
|---|---|---|---|---|---|---|---|---|---|---|---|
| | | Ethanal | Propanal | Butanal | Pentanal | Hexanal | Heptanal | Octanal | Nonanal | Decanal | Total |
| 0 | No. 1 | 2.20 | 0.00 | 0.20 | 2.65 | 0.00 | 0.00 | 0.00 | 0.15 | 0.00 | 5.20 |
| | No. 2 | 1.45 | 0.00 | 0.00 | 0.50 | 0.00 | 0.00 | 0.05 | 0.00 | 0.00 | 2.00 |
| | No. 3 | 0.00 | 0.00 | 0.00 | 0.35 | 0.00 | 0.25 | 0.15 | 0.10 | 0.20 | 1.05 |
| | No. 4 | 0.00 | 0.00 | 0.63 | 0.28 | 0.30 | 0.00 | 0.00 | 0.00 | 0.00 | 1.20 |
| 7 | No. 1 | 0.00 | 4.77 | 4.43 | 2.03 | 0.47 | 0.00 | 0.30 | 0.30 | 0.00 | 12.03 |
| | No. 2 | 0.55 | 0.00 | 0.00 | 0.12 | 5.52 | 0.00 | 0.05 | 0.00 | 0.29 | 7.53 |
| | No. 3 | 0.00 | 0.00 | 1.16 | 0.60 | 2.52 | 0.28 | 0.00 | 0.00 | 0.32 | 5.44 |
| | No. 4 | 0.00 | 0.00 | 2.48 | 1.12 | 0.00 | 0.78 | 0.12 | 0.00 | 0.00 | 4.50 |
| 14 | No. 1 | 0.00 | 4.28 | 9.70 | 5.89 | 0.73 | 0.00 | 0.38 | 0.00 | 0.00 | 20.98 |
| | No. 2 | 0.65 | 0.00 | 0.00 | 4.12 | 5.33 | 0.00 | 0.06 | 0.00 | 0.55 | 10.71 |
| | No. 3 | 0.00 | 0.00 | 0.00 | 2.06 | 2.76 | 0.33 | 0.00 | 0.00 | 0.29 | 5.44 |
| | No. 4 | 0.00 | 2.39 | 2.39 | 0.00 | 0.24 | 0.89 | 0.55 | 0.00 | 0.00 | 6.28 |

As evident from the results in Table 21, the formation level of volatile aldehydes from doughnuts changed depending on the types of coexisting saccharides. The system with trehalose less formed volatile aldehydes than that with sucrose, revealing that trehalose satisfactorily inhibited the formation of volatile aldehydes.

In more detail, the inhibition of the formation of volatile aldehydes by trehalose is attained both by incorporating trehalose into doughs of doughnuts and by spraying aqueous trehalose solutions over the surface of the doughnuts just after the processings without incorporating trehalose into the doughs. Particularly, it was revealed that spraying aqueous trehalose solutions over the surface of doughnuts just after the processings showed a higher inhibitory effect.

The following Examples A and B concretely describe in detail the present preferred examples of agents which inhibit the formation of volatile aldehydes and/or the decomposition of fatty acids, and of fatty-acid containing compositions.

EXAMPLE A-1 Agent for Inhibiting the Formation of Volatile Aldehydes and/or the Decomposition of Fatty Acids "MALSTAR®", a high maltose content syrup commercialized by Hayashibara Shoji, Inc., Okayama, Japan, was prepared into an about 40% solution by the addition of water. The solution was admixed with two units/g of a maltose/trehalose converting enzyme as disclosed in Japanese Patent Kokai No. 170,977/95, and allowed to react at 35° C. and pH 7.0 for 16 hours. The reaction mixture was in a usual manner heated to inactivate the remaining enzyme, decolored, purified, and concentrated into a syrupy product having a DE (dextrose equivalent) 42 and a moisture content of about 30%, and containing reducing saccharides such as glucose and maltose along with about 20% trehalose with respect to the syrup. The product is easily handleable and stable at ambient temperature, and it can be arbitrarily used as the captioned product of a syrupy inhibitory agent for preserving compositions with fatty acids and/or for processing materials thereof.

EXAMPLE A-2 Agent for Inhibiting the formation of volatile aldehydes and/or the Decomposition of Fatty Acids Corn starch was prepared into an about 30% suspension which was then subjected to the action of α-amylase to obtain a liquefied solution with a DE 15. To the solution were added five units/g starch of a non-reducing saccharide-forming enzyme as disclosed in Japanese Patent Kokai No. 213,283/95 and 10 units/g starch of a trehalose-releasing enzyme, and 50 units/g starch of an isoamylase, and the mixture was allowed to react at pH 6.0 and 40° C. for 24 hours. Thereafter, 10 units/g starch of β-amylase was added to the reaction mixture and enzymatically reacted for 10 hours. The resulting mixture was heated to inactivate the remaining enzyme, then in a usual manner decolored, desalted for purification, and concentrated into a syrupy product having a DE of about 38 and a mixture content of about 30% and containing reducing saccharides such as glucose, maltose, and maltotriose along with about 22% trehalose with respect to the syrup. The product is easily handleable and stable at ambient temperature, and it can be arbitrarily used as the captioned product of a syrupy inhibitory agent f or preserving compositions with fatty acids and/or for processing materials thereof.

EXAMPLE A-3

Agent for Inhibiting the Formation of Volatile Aldehydes and/or the Decomposition of Fatty Acids A syrup y product obtained by the method in Example A-2 was placed in an autoclave and admixed with 10% Raney nickel catalyst, followed by increasing the inner temperature to 90–120° C. under stirring conditions and increasing the inner hydrogen pressure to 20–120 kg/cm$^2$ to terminate the hydrogenation. Thereafter, the Raney nickel catalyst was removed from the reaction mixture, and the resulting mixture was in conventional manner decolored and desalted for purification, and concentrated into a syrupy product having a moisture content of about 30% W, DE of less than 1.0, and about 21% trehalose together with non-reducing saccharides such as sorbitol, maltitol, and maltotrutol. The product, having insubstantial reducibility, extremely-high stability, and relatively-high handleability, can be arbitrarily used as the captioned product of a syrupy inhibitory agent for preserving compositions with fatty acids and/or for processing materials thereof.

EXAMPLE A-4

Agent for Inhibiting the Formation of Volatile Aldehydes and/or the Decomposition of Fatty Acids In 100 parts by weight of water were dissolved by mixing 20 parts by weight of "TREHAOSE®", a hydrous crystalline trehalose commercialized by Hayashibara Shoji, Inc., Okayama, Japan, 10 parts by weight of sorbitol, 0.1 part by weight of calcium chloride, and 0.2 part by weight of citric acid. The resulting solution was placed in a container, sterilized by heating, and cooled into a syrupy product. The product can be arbitrarily used as the captioned product of a syrupy agent for preserving compositions with fatty acids and/or for processing materials thereof, particularly, it can be advantageously used for preserving edible parts of fishery products and/or for processing materials thereof.

EXAMPLE A-5

Agent for Inhibiting the Formation of Volatile Aldehydes and/or the Decomposition of Fatty Acids Fifty parts by weight of anhydrous crystalline trehalose commercialized by Hayashibara Shoji, Inc., Okayama, Japan, and 50 parts by weight of salt were mixed to homogeneity into a powdery product. The product can be arbitrarily used as the captioned product of a syrupy agent for preserving compositions with fatty acids and/or for processing materials thereof, particularly, it can be advantageously used for preserving edible parts of fishery products and/or for processing materials thereof.

EXAMPLE A-6

Agent for Inhibiting the Formation of Volatile Aldehydes and/or the Decomposition of Fatty Acids Twenty parts by weight of "TREHAOSE®", a hydrous crystalline trehalose commercialized by Hayashibara Shoji, Inc., Okayama, Japan, two parts by weight of "DEXYPEARL®", β-cyclodextrin powder commercialized by Hayashibara Shoji, Inc., Okayama, Japan, and one part by weight of pullulan were mixed to homogeneity. The resulting mixture was in conventional manner granulated by a granulator into granules. The product can be arbitrarily used as the captioned product of a syrupy agent for preserving compositions with fatty acids and/or for processing materials thereof.

EXAMPLE A-7

Agent for Inhibiting the Formation of Volatile Aldehydes and/or the Decomposition of Fatty Acids Twenty-five parts by weight of "TREHAOSE®", a hydrous crystalline trehalose commercialized by Hayashibara Shoji, Inc., Okayama, Japan, 25 parts by weight of "MABIT®", an anhydrous crystalline maltitol commercialized by Hayashibara Shoji, Inc., Okayama, Japan, one part by weight of pullulan, 0.1 part by weight of tartaric acid, and 0.1 part by weight of malic acid were mixed to homogeneity. The resulting mixture was in conventional manner tabletted by a tabletting machine into tablets, 8 mm in diameter and 4.5 mm thickness each. The product can be arbitrarily used as the captioned product of an inhibitory agent in the form of a tablet for preserving compositions with fatty acids and/or for processing materials thereof, particularly, it can be advantageously used for preserving edible parts of fishery products and/or for processing materials thereof.

EXAMPLE B-1

Processed Spawns

A syrupy inhibitory agent, obtained by the method in Example A-4, was placed in a container and diluted five-times with water. Fresh herring roes were placed in a bamboo basket and soaked in the above dilute. One hour after the soaking, the basket was taken out from the dilute for draining water to obtain the desired product. The product has properties of well-inhibiting trimethylamine formation, scarcely changing under cold storage, forming less drip even when thawed after cold storage, and well-keeping the original freshness during and after cold storage. Even after cooking of the product in a usual manner, it gave only a lesser smell of volatile aldehydes and trimethylamine, and had a satisfactory flavor, taste, and mouth feel.

EXAMPLE B-2

Dried Fish

One hundred parts by weight of a fillet of raw puffer was seasoned with a small amount of salt by homogeneously spraying over three parts by weight of a trimethylamine formation inhibitory agent containing salt obtained by the method in Example A-5, and rolled to extend plainly into a sheet with an about eight millimeters thickness. The sheet was soaked for 30 min in 200 parts by weight of a syrupy trimethylamine-formation-inhibitory agent obtained by the method in Example A-4, drained, and dried overnight into the desired product. The product less formed volatile aldehydes, well inhibited the decomposition of fatty acids, and satisfactorily maintained the original freshness. Even after grilled over a slow fire in a usual manner, the product gave a lesser smell of volatile aldehydes, trimethylamine, and ethyl mercaptan, and had a satisfactory flavor, taste, and mouth feel.

EXAMPLE B-3

Dried Small Sardine

After boiling 100 parts by weight of water in a caldron, two parts by weight of a trimethylamine-formation-inhibitory granule agent, obtained by the method in Example A-6, was dissolved and boiled therein, followed by soaking and boiling up therein 10 parts by weight of a raw Japanese anchovy placed in a bamboo basket. Thereafter, the boiled Japanese anchovy was taken out from the basket and dried in conventional manner into the desired product. The product, which the formation of volatile aldehydes and/or the decomposition of fatty acids are effectively inhibited, can be satisfactorily used to prepare a good stock with a satisfactory color tint, flavor, and taste.

EXAMPLE B-4

Dried small sardine

A Japanese anchovy, which had been boiled up by the method in Example B-3 and placed in a bamboo basket, was soaked for five minutes in a caldron with a boiling solution of 100 parts by weight of water dissolving 60 parts by weight of "TREHAOSE®", a hydrous crystalline trehalose commercialized by Hayashibara Shoji, Inc., Okayama, Japan. Thereafter, the boiled Japanese anchovy was taken out from the basket and dried in conventional manner into the desired product with crystallized hydrous trehalose crystal. The product, which the formation of volatile aldehydes and/or the decomposition of fatty acids are effectively inhibited, can be satisfactorily used to prepare a good stock with a satisfactory color tint, flavor, and taste. The product, having a lesser hygroscopicity, higher stability, and satisfactory sweetness, can be arbitrarily used as a delicacy, snack food, confectionery-type food, health food, etc.

EXAMPLE B-5

Shucked Short-Necked Clam

After boiling 100 parts by weight of water in a caldron, it was mixed with three parts by weight of a syrupy trimethylamine inhibitory agent obtained by the method in Example A-3, and boiled up. In the resulting solution was soaked and boiled up 10 parts by weight of short-necked clams placed in a bamboo basket. The clams were taken out from the basket and treated in conventional manner to obtain shucked short-necked clams boiled in water. The formation of volatile aldehydes and/or the decomposition of fatty acids in the product are well inhibited, and the product has a satisfactory color, gloss, flavor, and taste. The product can be arbitrarily processed into a food boiled down in soy and used as a material for seasoning for a seafood curry and a boiled rice mixed with fish and vegetables.

EXAMPLE B-6

Boiled Octopus

Ten parts by weight of raw octopus was seasoned with salt using a powdery trimethylamine formation inhibitory agent containing salt obtained by the method in Example A-5, and the resulting octopus was placed for boiling up in a caldron which contained 100 parts by weight of boiling water dissolving three parts by weight of a trimethylamine formation inhibitory agent in the form of a tablet obtained by the method in Example A-7. Thus, the desired product was obtained. The formation of volatile aldehydes and/or the decomposition of fatty acids of the product are well inhibited, and the product has a satisfactory color, gloss, flavor, and taste. Also it can be cut into slices in an appropriate size for use as a material of sushi, and arbitrarily used in daily dishes such as foods seasoned with vinegar and Japanese hotchpotch.

EXAMPLE B-7

Pacific Herring Seasoned with Vinegar

A fillet of raw Pacific herring was slightly seasoned with a powdery trimethylamine formation inhibitory agent obtained by the method in Example A-5, and after one-hour standing the seasoned fillet was soaked for five hours at ambient temperature in a seasoning, prepared by dissolving in 100 parts by weight of vinegar five parts by weight of a syrupy inhibitory agent obtained by the method in Example A-1 and one part by weight of a broth of tangle. The formation of volatile aldehydes and/or the decomposition of fatty acids in the product are well inhibited. The product has a satisfactory color, gloss, flavor, and taste, and it can be cut into slices with an appropriate size for use as a material of sushi and arbitrarily used in daily dishes or foods seasoned with vinegar.

EXAMPLE B-8

Yellowtail Boiled Hard with Soy

One hundred parts by weight of slices of fresh raw yellowtail was placed in a pan and boiled in a usual manner after mixed with 10 parts by weight of a syrupy inhibitory agent obtained by the method in Example A-2, 10 parts by weight of soy, five parts by weight of a sweet sake, and 10 parts by weight of water. The formation of volatile aldehydes and/or the decomposition of fatty acids in the product are well inhibited, and it has a satisfactory color, gloss, flavor, and taste.

EXAMPLE B-9

Fish Paste

Four thousand parts by weight of a thawed paste of Alaska pollack was pasted after mixing with 100 parts by weight of an aqueous solution which had been prepared by dissolving in water 80 parts by weight of an inhibitory granule agent obtained by the method in Example A-6, 80 parts by weight of sodium glutamate, 200 parts by weight of potato starch, 300 parts by weight of ice water, 12 parts by weight of sodium tripolyphosphate, 120 parts by weight of salt, and 10 parts by weight of maltitol. One hundred and twenty grams aliquots of the resulting paste were shaped and attached on wooden plates. The plates with paste were heated by steaming and steamed up until the inner temperature of the paste increased to about 80° C. in 30 min. Thereafter, the plates were cooled at ambient temperature and allowed to stand at 4° C. for 24 hours to obtain the desired product. The formation of volatile aldehydes and/or the decomposition of fatty acids are well inhibited, and the product has a satisfactory flavor and taste, fine surface, smooth gloss, and mouth feel.

EXAMPLE B-10

Peanut Cream

To 55 parts by weight of a syrupy inhibitory agent, obtained by the method in Example A-3 under heating conditions were homogeneously added and dissolved therein 12 parts by weight of a peanut butter, six parts by weight of a shortening, five parts by weight of an unsweetened condensed milk, 0.4 part by weight of an emulsifier, 0.2 part by weight of salt, 0.5 part by weight of a viscosity-imparting agent, an adequate amount of a flavor, and 18 parts by weight of water. The resulting mixture was in a usual manner condensed by boiling and bottled to obtain a peanut cream.

The formation of volatile aldehydes and/or the decomposition of fatty acids in the product are well inhibited, and the product has a satisfactory color, gloss, flavor, and taste.

EXAMPLE B-11

Snuck Food-Style Vegetable Food

Fifty-five parts by weight of hydrous crystalline trehalose, 10 parts by weight of anhydrous crystalline maltitol, and 35 parts by weight of water were placed in a plain pun, and the mixture was dissolved by heating. The solution was admixed with five parts by weight of a purified soybeans and boiled under a normal pressure to heat the contents to about 140° C.

Five parts by weight of sliced pumpkins, about five millimeters thickness, were soaked in the above solution, heated until the solution was heated to about 145° C., took out in a bamboo basket, sprayed with a small amount of hydrous crystalline trehaose, allowed to stand at ambient temperature overnight to obtain the captioned product with the saccharide crystals on its surface.

The formation of volatile aldehydes and/or the decomposition of fatty acids in the product are well inhibited, and the product has a satisfactory color, gloss, flavor, and taste.

EXAMPLE B-12

Refined Rice

One hundred parts by weight of unhulled rice (aged rice) were under mixing conditions sprayed with four parts by weight of a 25% aqueous trehalose solution, then allowed to stand at ambient temperature overnight, and subjected to a refiner to obtain a cleaned rice. The product contains about 0.2% trehalose and has a satisfactory quality and stability, while inhibiting the formation of volatile aldehydes and/or the decomposition of fatty acids. The product can be arbitrarily used as a material for cooked rice, rice ball, gullet, etc., and used intact as a pre-washed rice and processed into pre-gelatinized rice. Rice bran, obtained as a byproduct of the process for refining rice, contains trehalose, well inhibits the formation of volatile aldehydes and/or the decomposition of fatty acids, and has a satisfactory stability, so that it can be arbitrarily used as a material for pickles with rice lees, premix of rice bran, and oils of rice lees, and used as a feed composition without any processing or after defatted into a defatted lees.

EXAMPLE B-13

Pre-Washed Rice

One hundred parts by weight of unhulled rice just after refining were mixed with one part by weight of a hydrous crystalline trehalose powder, and the mixture was stored in a storeroom for six months, and then subjected to a rice refiner to obtain a cleaned rice. The cleaned rice was transferred on an endless belt made of wire netting, washed by spraying with a high-pressure sprinkler in a quite short time while mixing and moving the cleaned rice, sprayed with one part by weight of an aqueous solution containing one percent of calcium lactate and 20% of an inhibitory granule agent obtained by the method in Example A-6, dried, weighed, and injected into a container to obtain a pre-washed rice. The product is a high-quality pre-washed rice which contains about 0.3% trehalose, well inhibits the formation of volatile aldehydes and/or the decomposition of fatty acids, and has a satisfactory stability, so that it can be arbitrarily used in cocked rice, rice ball, and gullet to impart them a satisfactory flavor and enrich them with calcium. Thus the product can be satisfactorily used to maintain and promote the health.

EXAMPLE B-14

Koji

A refined rice, obtained by the method in Example B-12, was soaked in water at ambient temperature for five hours, placed in a basket, placed in a steamer, steamed up, spread over a sheet, cooled to about 35° C., and mixed with an about 0.1% of a culture of the species of *Aspergillus orizae* as a koji. The mixture was placed in a vat, and cultured for two days in an incubator at 27° C. while keeping the contents to give a temperature of about 30 to about 38° C. to obtain a koji. The product was a high-quality koji having a satisfactory color, fermentability, flavor and taste, so that it can be arbitrarily used in producing fermented food products such as a sweet drink made from fermented rice, sake, miso, soy sauce, pickles with koji, etc.

EXAMPLE B-15

Sweet Drink Made from Fermented Rice

Ten parts by weight of a cleaned rice obtained by the method in Example B-12 were steamed up after admixed with water in a usual manner. The cooked rice was cooled to 55° C., admixed with 30 parts by weight of a koji obtained by the method in Example B-14 and 0.1 part by weight salt, followed by an incubation at 50–55° C. for eight hours. The resulting mixture was subjected to a mixer, packed in a small bag, and sterilized into a sweet drink made from fermented rice. The product was a high-quality sweet drink having a satisfactory color, flavor and taste.

EXAMPLE B-16

Radish Pickled with Lees

Three thousands parts by weight of radishes were pickled with a small amount of salt in a usual manner, then successively pickled with one part by weight of saccharin sodium, and pickled in a composition consisting of 170 parts by weight of rice lees containing trehalose obtained by the method in Example B-12, one part by weight of saccharin sodium, three parts by weight of glycine, 20 parts by weight of sodium glutamate, seven parts by weight of a complex seasoning, 50 parts by weight of a hydrogenated starch syrup, 36 parts by weight of salt, six parts by weight of ethanol, and 50 parts by weight of a 10% pullulan solution to obtain the captioned product. The product was a high-quality radish pickled with koji having a satisfactory color, gloss, flavor, taste, and mouth feel.

EXAMPLE B-17

Wheat Flour

One hundred parts by weight of a high-quality wheat were admixed by spraying with two parts by weight of a 20% aqueous trehalose solution. The mixture was in a usual manner ground into a wheat flour. The product was a high-quality wheat flour containing about 0.3% trehalose, which well inhibited the formation of volatile aldehydes and/or the decomposition of fatty acids and had a satisfactory stability. The product can be arbitrarily used in producing confectioneries, bakeries, pastas, noodles, frozen-pizzas, and premixes. Wheat brans, obtained as a byproduct during the grinding step, contained trehalose, well inhibited the formation of volatile aldehydes and/or the decomposition of fatty acids, and had a satisfactory stability, so that it can be arbitrarily used as a material for oils of wheat embryo buds and for feed compositions.

EXAMPLE B-18

Salad Oil

One hundred parts by weight of high-quality soybeans were pressed, admixed to homogeneity as much as possible by spraying with two parts by weight of an aqueous solution with a saccharide concentration of about 25%, prepared by diluting with water a syrupy inhibitory agent obtained by the method in Example A-3. The mixture was in a usual manner treated by heating, treated with n-hexane as a solvent to extract lipids, distilled in vacuo to remove the solvent, removed gums, desalted, decolored, removed smells, and purified by steps including wintering to obtain a salad oil. During the process for purifying oils, the formation of volatile aldehydes and/or the decomposition of fatty acids were well inhibited, and this facilitated the production of a high-quality salad oil. Since the product thus obtained has a satisfactory quality and shelf-life, it can be arbitrarily used as an oil and fat for tempuras, fryings, mayonnaises, and dressings. Defatted soybeans obtained as a byproduct in the processing step contain trehalose, so that they effectively inhibit the formation of volatile aldehydes and/or the decomposition of fatty acids and have a satisfactory shelf-life. Thus, they can be arbitrarily used as materials for tofus, fried bean curds, soybean flours, miso, soy sauce, and feed compositions.

EXAMPLE B-19

Mayonnaise

Seventeen parts by weight of egg yolks, 13 parts by weight of vinegar, three parts by weight of a powdery inhibitory agent obtained by the method in Example A-5, one part by weight of sugar, one parts by weight of a spice, and 65 parts by weight of a salad oil were placed in a mixer and mixed by stirring. The resulting mixture was in a usual manner subjected to a homogenizer, filtered, and injected into a container to obtain a mayonnaise. The product is a high-quality mayonnaise which has a satisfactory color, flavor, taste, and shelf-life, and well inhibits the formation of volatile aldehydes and/or the decomposition of fatty acids.

EXAMPLE B-20

Powdered Egg Yolk

Egg yolks prepared from fresh eggs were sterilized at 60–64° C. on a plate-type heat sterilizer. To one part by weight of the resulting liquid egg yolk, five parts by weight of an anhydrous crystalline trehalose powder were added, and the mixture was pulverized into a powdery egg york. The product, which the formation of volatile aldehydes and/or the decomposition of fatty acids are well inhibited and maintains stably the original quality, so that it can be arbitrarily used as a material for confectionery such as a premix, frozen dessert, emulsifier, etc., as well as a food for infants and therapeutic nutritions such as oral liquid foods, and intubation liquid foods. Also it can be arbitrarily used as a skin-beautifying agent and hair restorer.

EXAMPLE B-21

Powdered Oils and Fats

To 150 parts by weight of a soybean salad oil and one part by weight of lecithin was added 20 parts by weight of water, and the resulting mixture was admixed with 10 parts by weight of anhydrous crystalline trehalose to convert the crystal into hydrous crystalline trehalose. The hydrous crystal was then pulverized and sieved into a high-quality powder containing the salad oil. The product effectively inhibits the formation of volatile aldehydes and/or the decomposition of fatty acids and has a satisfactory shelf-life, so that it can be arbitrarily used as a material for confectioneries such as premixes, frozen candies, sponge cakes, candies, etc.; for seasonings such as mayonnaises, dressings, potages, soups, stews, rice fries, etc.; for therapeutic nutrients such as hyper alimentaries for intubation feeding; and for feed compositions.

EXAMPLE B-22

Powdery Composition of Emulsifier

Thirty parts by weight of sucrose fatty acid ester, 10 parts by weight of glyceryl monofatty acid ester, 10 parts by weight of sorbitan monofatty acid ester, 30 parts by weight of "FINETOSE®", anhydrous crystalline maltose commercialized by Hayashibara Shoji Inc., Okayama, Japan, and 35 parts by weight of water were mixed by heating at 90–95° C. into a homogenous pasted emulsifier composition. The composition was admixed with 80 parts by weight of a crystalline a-maltose powder and 100 parts by weight of anhydrous crystalline trehalose, and the mixture was aged and pulverized to obtain the captioned product. The product has a sufficient emulsifying- and foaming-power, well inhibits the formation of volatile aldehydes and/or the decomposition of fatty acids, and has a satisfactory shelf-life. Also the product can be extensively used in food processings of confectioneries, bakeries, etc.; cosmetics such as detergents; and pharmaceuticals such as dispersants. Foods with the product such as sponges and bakeries are superior in appearance, physical property, quality, flavor and taste.

EXAMPLE B-23

Premix for Food

One hundred parts by weight of wheat flour, 70 parts by weight of sugar, 40 parts by weight of hydrous crystalline trehalose, six parts by weight of a powdery composition of an emulsifier obtained by the method in Example B-22, two parts by weight of skim milk, and 0.15 part by weight of a vanilla flavor were mixed to homogeneity. The mixture was injected into bags in a prescribed amount for a premix powder used in confectioneries. The product well inhibits the formation of volatile aldehydes and/or the decomposition of fatty acids, and has a satisfactory shelf-life.

A sponge cake was prepared by adding both 70 parts by weight of eggs and 14 parts by weight of water to 100 parts by weight of the above premix powder, whipping the mixture in a usual manner, pouring the resultant mixture into a mold, and baking the content. The sponge cake has a fine texture, satisfactory mouth feel, flavor and taste.

EXAMPLE B-24

Roasted Almond

One hundred parts by weight of select almonds were in a usual manner roasted, and then admixed to homogeneity as much as possible by spraying with two parts by weight of an aqueous solution with a saccharide concentration of about 20%, prepared by diluting with water a powdery inhibitory agent obtained by the method in Example A-5 while the roasted almonds still having a relatively-high temperature were stirring, and sprayed with powdery salt to obtain roasted almonds. The almonds have a satisfactory flavor, taste, and shelf-life, and effectively inhibit the formation of volatile aldehydes and/or the decomposition of fatty acids; they can be in themselves tasted as snacks and arbitrarily used as materials for processing confectioneries and bakeries.

EXAMPLE B-25

Roasted Almond Slice

Commercially available sliced almonds, about one millimeter thickness, were soaked in an about 70% aqueous trehalose solution heated to 70° C., for 10 min, and then drained and roasted using an electric oven to obtain the captioned product having a satisfactory color tint, texture, flavor and taste. The product effectively inhibits the formation of volatile aldehydes and/or the decomposition of fatty acids, and has a satisfactory shelf-life; it can be tasted intact as a snack and used as a material for processing confectioneries and bakeries. The product is an almond covered with a colorless and transparent trehalose candy and a superior quality.

EXAMPLE B-26

Fried Banana Fried In Vacuo

A banana was pealed, cut with a cutter into slices of banana, about one centimeter thickness, which were then soaked in an about 40% aqueous trehalose solution heated to 50° C. for 10 min, drained, and fried in vacuo using oils and fats for food in a usual manner to obtain the captioned product with a satisfactory shape, color tint, texture, flavor and taste. In the product, the formation of volatile aldehydes and/or the decomposition of fatty acids are well inhibited, it can be tasted intact as a snack and used as a material for processing confectioneries and bakeries.

EXAMPLE B-27

Fried Apple Fried In Vacuo

An apple was washed and cut with a cutter into slices of apple, about five millimeters thickness, which were then soaked for 15 min in an aqueous solution with a saccharide concentration of about 30% and a salt concentration of about 0.1%, which had been prepared by diluting a syrupy inhibitory agent obtained by the method in Example A-3 with water and adding salt to the resulting solution, drained, and preserved by freezing at −20° C. The slices were in a usual manner fried in vacuo using oils and fats for food to obtain the captioned product with a satisfactory shape, color tint, texture, flavor and taste. In the product, the formation of volatile aldehydes and/or the decomposition of fatty acids are well inhibited, it can be tasted intact as a snack and used as a material for processing confectioneries and bakeries.

EXAMPLE B-28

Fried Carrot Fried In Vacuo

A carrot was pealed and cut with a cutter into slices, about five millimeters thickness, which were then soaked for 20 min in an aqueous solution, which had been heated to 60° C. and had a trehalose concentration of about 40% and a salt concentration of about 0.1%, drained and subjected to blanching for two minutes. The slices were in a usual manner fried in vacuo using oils and fats for food to obtain the captioned product with a satisfactory shape, color tint, texture, flavor and taste. In the product, the formation of volatile aldehydes and/or the decomposition of fatty acids are well inhibited, it can be tasted intact as a snack and used as a material for processing confectioneries and bakeries, and for instant foods.

EXAMPLE B-29

Fried Potato

Potatoes were washed, sliced by a slicer into square cubes, about one centimeter each side, which were then soaked in for 20 min an aqueous solution, which had been heated to 50° C. and had a trehalose concentration of about 30% and a salt concentration of about 0.1%, drained, subjected to blanching for three minutes, and preserved by freezing at −20° C. The slices were in a usual manner fried in vacuo to obtain the captioned product with a satisfactory shape, color tint, texture, flavor and taste. In the product, the formation of volatile aldehydes and/or the decomposition of fatty acids are well inhibited, it can be tasted intact as a snack and arbitrarily used as a daily dish.

EXAMPLE B-30

Ice Cream

Eighteen parts by weight of a raw cream containing about 46% oils and fats, seven parts by weight of skim milk, 51 parts by weight of whole milk, eight parts by weight of sugar, six parts by weight of hydrous crystalline trehalose, four parts by weight of "NYUKA OLIGO®", a lactosucrose powder, three parts by weight of a black kneaded sesame, one part by weight of pullulan, and two parts by weight of gum arabic were mixed into a solution. Then, the solution was sterilized by incubating at 70° C. for 30 min, emulsified and dispersed by a homogenizer, instantly cooled to 3–4° C., allowed to stand overnight for aging, and freezed by a freezer into an ice cream. The product is a sesame-flavored ice cream, which the formation of volatile aldehydes and/or the decomposition of fatty acids are well inhibited, and has a satisfactory shelf-life, mouth feel, and overrun, so that it can be arbitrarily used as a health food with a growth promoting activity of bifid bacteria.

EXAMPLE B-31

Wheat Water

One hundred parts by weight of select burley were in a usual manner roasted, and the heated roasted burley was sprayed by mixing with two parts by weight of a 10% aqueous trehalose solution, dried by ventilation, injected into a small bag, and packed into a tea bag for wheat water. The product has a satisfactory flavor, taste and shelf-life. The formation of volatile aldehydes and/or the decomposition of fatty acids in the product are well prevented.

EXAMPLE B-32

Green Tea Beverage

Three parts by weight of a green tea were extracted with 180 parts by weight of hot water, and the extract was admixed with and allowed dissolve L-ascorbic acid, "αG RUTIN", α-glycosyl rutin commercialized by Hayashibara Shoji, Inc., Okayama, Japan, to give respective concentrations of 0.05 w/v %, 0.01 w/v %, and 0.7 w/v %. The resulting mixture was injected into a 500-ml plastic transparent bottle and sterilized into a bottled green tea beverage. The product has a satisfactory color tint, flavor and taste of green tea, and has a relatively-long shelf-life. The formation of volatile aldehydes and/or the decomposition of fatty acids in the product are well prevented.

EXAMPLE B-33

Feed Composition

Thirty parts by weight of powdered bran, 35 parts by weight of skim milk, 10 parts by weight of rice bran as a byproduct obtained by the method in Example B-12, 10 parts by weight of a high lactosucrose content powder, 10 parts by weight of a vitamin agent, five parts by weight of a fish meal, five parts by weight of monohydrogenphosphate, three parts by weight of liquid oils and fats, three parts by weight of calcium carbonate, two parts by weight of salt, two parts by weight of anhydrous crystalline trehalose, and two parts by weight of a mineral agent were mixed to obtain a feed composition. The product having a satisfactory shelf-life is a feed for domestic animals including poultry, particularly, for infant pigs. The formation of volatile aldehydes and/or the decomposition of fatty acids in the product are well prevented. Since the product effectively promotes the growth of bifid bacteria and the mineral absorption, it can be advantageously used to prevent domestic animals from infection and diarrhea, promote the growth, and prevent disagreeable smells of feces. Depending on use, the product can be prepared into another type feed-composition by combining with condensed feed materials such as cereals, wheat flours, starches, oil cakes, lees and brans; and crude feed materials such as straws, hays, bagasse, and corncobs.

EXAMPLE B-34

Soap

To 96.5 parts by weight of a neat soap prepared by saponifying and salting out tallow and oil palm (=4:1 by weight) in a usual manner were added 1.5 parts by weight of hydrous crystalline trehalose, 0.5 part by weight of 2-O-α-D-glucosyl-L-ascorbic acid, 0.5 part by weight of refined sugar, one part by weight of maltitol, 0.0001 part by weight of Kankoso 201 (a photosensitizing pigment), and an adequate amount of a flavor. The mixture was mixed to homogeneity, poured into a mould, cooled and solidified into a soap.

The product is a soap which the formation of volatile aldehydes and/or the decomposition of fatty acids in the product are well prevented, and which stably maintains its original high-quality. Since the product effectively inhibits the formation of volatile aldehydes from sweat, dirt and sebum and/or the decomposition of fatty acids from sweat, dirt, and sebum, it can be arbitrarily used as a soap to prevent from causing body smells and itches.

EXAMPLE B-35

Cosmetic Milky Lotion

A half part by weight of polyoxyethylene behenyl ether, 1.0 part by weight of polyoxyethylene sorbitol tetraoleate, 1.0 parts by weight of oil-soluble glyceryl monostearate, 0.5 part by weight of behenyl alcohol, 1.0 part by weight of avocado oil, 0.1 part by weight of linoleic acid, and adequate amounts of vitamin E and an antiseptic were in a usual manner dissolved by heating into a solution. To the solution were added 5.0 parts by weight of 1,3-butyleneglycoal, 3.5 parts by weight of sodium L-lactate, 3.0 parts by weight of a syrupy inhibitory agent obtained by the method in Example A-3, 0.1 part by weight of carboxyvinylpolymer, and 80.3 parts by weight of refined water. The resulting mixture was emulsified by a homogenizer and admixed with an adequate amount of a flavor under stirring conditions into a milky lotion.

The product, which the formation of volatile aldehydes and/or the decomposition of fatty acids are well inhibited, is a skin whitening agent with a stabilized high-quality. Also it can be arbitrarily used as agents for treating and preventing dyspigmentation such as liver spots, freckles, and sunburn.

EXAMPLE B-36

Cosmetic Cream

Two parts by weight of polyoxyetgyleneglycoal monostearate, five parts by weight of self-emulsifying glyceryl monostearate, five parts by weight of potassium DL-lactate, one parts by weight of behenyl alcohol, 2.0 parts by weight of eicosatetraenoic acid, one part by weight of liquid petrolatum, 10 parts by weight of glyceryl trioctanate, and an adequate amount of an antiseptic were in a usual manner dissolved by heating. The resulting solution was admixed with two parts by weight of hydrous crystalline trehalose, five parts by weight of 1,3-butyleneglycoal, and 66 parts by weight of refined water. The mixture thus obtained was emulsified by a homogenizer and admixed with an adequate amount of a flavor under stirring conditions to obtain a cream.

The product, which the formation of volatile aldehydes and/or the decomposition of fatty acids are well inhibited, is a skin whitening agent with a stabilized high-quality. Since the product effectively inhibits the formation of volatile aldehydes from sweat, dirt, dandruff and skin fat and/or the decomposition of fatty acids from sweat, dirt, dandruff and skin fat are well inhibited, it can be arbitrarily used to prevent from causing body smells, skin stimulation, and itches, and also used in the treatment and/or the prevention of dyspigmentation such as liver spots, freckles, and sunburn.

EXAMPLE B-37

Cosmetic Cream

Two parts by weight of polyoxyethyleneglycoal monostearate, five parts by weight of self-emulsifying glyceryl monostearate, five parts by weight of potassium DL-lactate, one parts by weight of behenyl alcohol, 2.0 parts by weight of eicosatetraenoic acid, one part by weight of liquid petrolatum, 10 parts by weight of glyceryl trioctanate, and an adequate amount of an antiseptic were in a usual manner dissolved by heating. The resulting solution was admixed with 1.6 parts by weight of hydrous crystalline trehalose, 0.1 part by weight of sodium hyaluronate, 0.1 part by weight of dipotassium glycyrrhetinic acid, 0.1 part by weight of an Aloe vera extract, 0.05 part by weight of a Melissa extract, 0.05 part by weight of camomile extract, five parts by weight of 1,3-butyleneglycoal, and 66 parts by weight of refined water. The mixture thus obtained was emulsified by a homogenizer and admixed with an adequate amount of a flavor under stirring conditions to obtain a cream.

The product, which the formation of volatile aldehydes and/or the decomposition of fatty acids are well inhibited, is a skin whitening agent with a stabilized high-quality. Since the product effectively inhibits the formation of volatile aldehydes from sweat, dirt, dandruff and skin fat and/or the decomposition of fatty acids from sweat, dirt, dandruff and skin fat are well inhibited, it can be arbitrarily used to prevent from causing body smells, skin stimulation, and itches, and also used in the treatment and/or the prevention of dyspigmentation such as liver spots, freckles, and sunburn. Since the product has a superior moisture-maintaining ability and less stimulate the skin, it can be arbitrarily used with a lesser fear of hypersensitivity.

EXAMPLE B-38

Lipid Emulsion for Injection

Ten parts by weight of soybean oil, 1.0 part by weight of soybean lecithin, 90 parts by weight of water, and 10 parts by weight of hydrous crystalline trehalose were stirred by mixing with a mixer for 10 min to obtain a crude emulsion. The emulsion was then homogenized by a pressure-injection-type emulsifier, commercialized by Mantle Gorlin, Sweden, under a flux of nitrogen gas at a pressure of 600 kg/cm$^2$ into an oil in water type of micro-granular agent with an average granular size of not higher than 0.2$\mu$. Then, the agent was in a usual manner sterilized using a membrane filter, and the filtrate was distributed to injection vials, followed by sealing and sterilizing by heating the vials into a lipid emulsion for an intravenous injection.

The formation of volatile aldehydes and/or the decomposition of fatty acids in the product are well inhibited, and the quality of the product is also stably maintained. Also the product can be arbitrarily used as an oral or intubation fluid food.

EXAMPLE B-39

Nutrient

Five hundred parts by weight of anhydrous crystalline trehalose, 190 parts by weight of a powdery egg yolk obtained by the method in Example B-20, 200 parts by weight of skim milk, 100 parts by weight of a powdery oil and fat obtained by the method in Example B-21, 4.4 parts by weight of sodium chloride, 1.85 parts by weight of potassium chloride, four parts by weight of magnesium sulfate, 0.01 part by weight of thiamine, 0.1 part by weight of sodium ascorbate, 0.6 part by weight of vitamin E acetate, and 0.04 part by weight of nicotinic acid amide were mixed to obtain a composition. Twenty-five grams aliquots of the composition were injected into small laminated aluminum bags which were then heat sealed to obtain a nutrition that is used by dissolving in a solvent before use. Since the formation of volatile aldehydes and/or the decomposition of fatty acids in the product are well inhibited, and the product has a satisfactory stability at ambient temperature, it needs no storage under cooling conditions. The product has a satisfactory solubility and dispersibility. With these features, the product can be arbitrarily used to easily supplement calories and nutritions to the living bodies by dissolving one bag in about 150 to about 300 ml hot water and administering the solution to subjects, and used to maintain the health, promote the growth, promote the prevention and treatment of diseases, and recover the health conditions from fatigues after physical activities, and promote the health. Also the product can be used for not only humans but domestic animals as an orally and/or intubationally administrable composition.

As described above, completely differing from prior arts, the present invention is to provide a method for inhibiting the formation of volatile aldehydes per se from fatty acids and compositions containing the same and/or the decomposition of fatty acids per se, compositions prepared therewith, agents for inhibiting the formation of volatile aldehydes and/or the decomposition of fatty acids, which comprises as effective ingredient trehalose and/or maltitol; and uses thereof. Since trehalose and/or maltitol are stable non-reducing saccharides, nutritional and tastable ingredients such as vitamins, amino acids, peptides, etc., which are contained in fatty acids or compositions containing the same such as foods, cosmetics, and pharmaceuticals, and their materials or intermediates are scarcely destroyed, and the saccharides impart a relatively-high quality to the compositions prepared therewith as a merit. Thus, the establishment of the present invention provides a novel preservation and/or processing for fatty acids and/or compositions containing the same, and also provides compositions such as foods, cosmetics, and pharmaceuticals with a relatively-high quality and stability in actual uses. Therefore, it is unfathomable the influence of the present invention on the fields, particularly, on agricultures, forestry, livestocks, fisheries, food products, health foods, cosmetics, and pharmaceuticals.

While there has been described what is at present considered to be the preferred embodiments of the invention, it will be understood the various modifications may be made therein, and it is intended to cover the appended claims all such modifications as fall within the true spirits and scope of the invention.

We claim:

1. A method for inhibiting the formation of a volatile aldehyde and its related compound and/or the decomposition of a fatty acid and its related compound, which comprises
    incorporating trehalose with or without maltitol into a product to be treated containing said fatty acid and/or its related compound, in a total amount of said trehalose and maltitol of at least about 0.01 w/w % to said fatty acid and/or its related compound, on a dry solid basis.

2. A method for inhibiting the formation of a volatile aldehyde and its related compound and/or the decomposition of a fatty acid and its related compound, which comprises:
    preserving and/or processing a product comprising said fatty acid and/or its related compound in the presence of trehalose with or without maltitol in a total amount of at least about 0.01 w/w % thereof to said fatty acid and/or its related compound, on a dry solid basis.

3. The method of claim 2, wherein said fatty acid and its related compound is a member selected from the group consisting of fatty acids, their salts and esters, and mixtures thereof.

4. The method of claim 2, wherein said fatty acid and its related compound is a higher fatty acid and its related compound.

5. The method of claim 2, wherein said trehalose and said maltitol are incorporated into said fatty acid and its related compound in a total amount of at least about 0.01 w/w % to said fatty acid and its related compound, on a dry solid basis, by one or more methods selected from the group consisting of dissolving, melting, dispersing, mixing, suspending, soaking, adhering, crystallizing, coating, and spraying.

6. The method of claim 2, wherein said volatile aldehyde and its related compound is one or more members selected from the group consisting of aldehydes with carbon atom numbers of 10 or lower.

7. The method of claim 2, which further inhibits the formation of trimethylamine and ethyl mercaptan, pH reduction, heat generation, browning, and/or weight reduction in compositions containing fatty acids and their related compounds.

8. A method for inhibiting the formation of volatile aldehydes and their related compounds and/or the decomposition of fatty acids and their related compounds, which comprises:

incorporating an agent into a product to be treated to provide in said product at least about 0.01 w/w % of trehalose and maltitol to said fatty acids and their related compounds, on a dry solid basis, said agent comprising trehalose with or without maltitol as an effective ingredient in a total amount of at least about 10 w/w %, on a dry solid basis.

9. A method for inhibiting the formation of volatile aldehydes and their related compounds and/or the decomposition of fatty acids and their related compounds, which comprises:

incorporating an agent into a fatty acid or a related compound to give at least about 0.01 w/w % of trehalose and maltitol to said fatty acid or its related compound, on a dry solid basis, by one or more methods selected from the group consisting of dissolving, melting, dispersing, mixing, suspending, soaking, adhering, crystallizing, coating, and spraying, said agent comprising trehalose with or without maltitol as an effective ingredient in a total amount of at least about 0.01 w/w % on a dry solid basis; and preserving and/or processing the resulting mixture.

10. A method for processing a fatty acid ester, which comprises a step of; in treating said fatty acid ester with one or more processing treatments selected from the group consisting of stirring, mixing, heating, pressing, separating, emulsifying, pulverizing, and drying;

incorporating into said fatty acid ester trehalose with or without maltitol in an amount of at least about 0.01 w/w % of trehalose and maltitol to said fatty acids and their related compounds, on a dry solid basis, or an agent before, during, or after the processing treatment to give at least about 0.01 w/w % of trehalose and maltitol to said fatty acids and their related compounds, on a dry solid basis, said agent comprising trehalose with or without maltitol as an effective ingredient in a total amount of at least about 10 w/w %, on a dry solid basis.

11. The method of claim 10, wherein said fatty acid ester is a member selected from the group consisting of oils and fats, lipids, emulsifiers, and mixtures thereof.

12. A method for processing a fishery product, which comprises a step of; in treating a fishery product with one or more processing treatments selected from the group consisting of drying, soaking, grilling, boiling, steaming, frying, and roasting;

incorporating into the fishery product trehalose with or without maltitol in an amount of at least about 0.01 w/w % of trehalose and maltitol, on a dry solid basis, or an agent before, during, or after the processing treatment to give at least about 0.01 w/w % of trehalose and maltitol to said fatty acids and their related compounds, on a dry solid basis, said agent comprising trehalose with or without maltitol as an effective ingredient in a total amount of at least about 10 w/w %, on a dry solid basis.

13. The method of claim 12, wherein said fishery product is an edible part of a fishery product selected from the group consisting of fishes, spawns, the Mollusca, cruschymata, shellfishes, and mixtures thereof.

14. A method for processing a seed, which comprises a step of; in treating a seed with one or more processing treatments selected from the group consisting of refining, milling, oil reining, boiling by steaming, and roasting;

incorporating into the seed trehalose with or without maltitol in an amount of at least about 0.01 w/w % of trehalose and maltitol, on a dry solid basis, or an agent before, during, or after the processing treatment to give at least about 0.01 w/w % of trehalose and maltitol to said fatty acids and their related compounds, on a dry solid basis, said agent comprising trehalose with or without maltitol as an effective ingredient in a total amount of at least about 10 w/w %, on a dry solid basis.

15. The method of claim 14, wherein said seed is a member selected from the group consisting of those of food oils, cereals, beans, relishes, and mixtures thereof.

16. A processed seed which is obtainable by a process comprising:

incorporating an agent into a seed to give at least about 0.01 w/w % of trehalose and maltitol to said fatty acids and their related compounds, on a dry solid basis, said agent comprising trehalose with or without maltitol as an effective ingredient in a total amount of at least about 10 w/w %, on a dry solid basis; and treating said seed with one or more processing selected from the group consisting of refining, powering, oil refining, steaming, and roasting.

17. The processed seed of claim 16, wherein said seed is a member selected from the group consisting of a rice, wheat, barley, rye, adlay, millet, buckwheat, sesame, soybean, peanut, almond, coffee bean, cocoa bean, and mixtures thereof.

18. The processed seed of claim 16, which is a member selected from the group consisting of a refined rice, rice with embryo bud, prewashed rice, refined barley, refined adlay, refined millet, powdered rice, wheat flour, barley flour, rye flour, adlay flour, buckwheat flour, soybean flour, ground sesame, powder of roasted grain, soybean flour, coarse cut coffee, unhulled rice tea, barley tea, adlay, and byproducts including rice lees, wheat lees, barley lees, defatted lees, defatted soybean, and mixtures thereof.

19. A method for inhibiting the formation of volatile aldehydes and their related compounds contained in a cleaned or unhulled rice and/or the decomposition of fatty acids and their related compounds contained in a cleaned or unhulled rice by incorporating into said cleaned or unhulled rice trehalose with or without maltitol in an amount of at least about 0.01 w/w % of trehalose and maltitol to said fatty acids and their related compounds, on a dry solid basis, or an agent to give at least about 0.01 w/w % of trehalose and maltitol to said fatty acids and their related compounds, on a dry solid basis, said agent comprising trehalose with or without maltitol as an effective ingredient in a total amount of at least about 10 w/w %, on a dry solid basis.

20. The method of claim 19, wherein said volatile aldehydes and their related compounds are ingredients of smells of rice lees and/or aged rice.

21. A method of preparing koji, which comprises:

boiling by steaming refined seeds into which trehalose with or without maltitol in an amount of at least about 0.01 w/w % of trehalose and maltitol, on a dry solid basis, or an agent has been incorporated to provide at least about 0.01 w/w % of trehalose and maltitol, on a dry solid basis, said agent comprising trehalose with or without maltitol as an effective ingredient in a total amount of at least 10 w/w %, on a dry solid basis;

cooling the steamed refined-seeds; and inoculating a seed of koji to the resulting seeds.

22. The method of claim 21, wherein said koji is a culture of a fungi of the species *Aspergillus orizae*.

23. A process for processing fruits/vegetables, which comprises the steps of; in treating fruits/vegetables with one or more processing treatments selected from the group consisting of drying, soaking, grilling, boiling, steaming, and frying;

incorporating into said fruits/vegetables trehalose with or without maltitol in an amount of at least about 0.01 w/w % of trehalose and maltitol, on a dry solid basis, or an agent before, during or after the processing treatment to give at least about 0.01 w/w % of trehalose and maltitol to said fatty acids and their related compounds, on a dry solid basis, said agent comprising trehalose with or without maltitol as an effective ingredient in a total amount of at least 10 w/w %, on a dry solid basis.

24. The method of claim 1 comprising said incorporating of said trehalose in an amount sufficient to inhibit the formation of a volatile aldehyde and insufficient to impart substantial sweetness to said product.

25. The method of claim 1 comprising said incorporating of said maltitol in an amount sufficient to inhibit the formation of a volatile aldehyde and insufficient to impart substantial sweetness to said product.

* * * * *